United States Patent
Zandinejad et al.

(10) Patent No.: US 10,716,648 B2
(45) Date of Patent: Jul. 21, 2020

(54) METHODS FOR FABRICATING DENTAL RESTORATIONS

(71) Applicant: University of Louisville Research Foundation, Inc., Louisville, KY (US)

(72) Inventors: Amirali Zandinejad, Louisville, KY (US); Wei-Shao Lin, Louisville, KY (US); Dean Morton, Louisville, KY (US)

(73) Assignee: University of Louisville Research Foundation, Inc., Louisvile, KY (US)

( * ) Notice: Subject to any disclaimer, the term of this patent is extended or adjusted under 35 U.S.C. 154(b) by 189 days.

(21) Appl. No.: 15/308,551

(22) PCT Filed: Apr. 30, 2015

(86) PCT No.: PCT/US2015/028629
§ 371 (c)(1),
(2) Date: Nov. 2, 2016

(87) PCT Pub. No.: WO2015/168463
PCT Pub. Date: Nov. 5, 2015

(65) Prior Publication Data
US 2017/0056138 A1 Mar. 2, 2017

Related U.S. Application Data

(60) Provisional application No. 61/987,643, filed on May 2, 2014.

(51) Int. Cl.
*A61C 13/00* (2006.01)
*A61C 5/77* (2017.01)
(Continued)

(52) U.S. Cl.
CPC ............ *A61C 13/0019* (2013.01); *A61C 5/77* (2017.02); *A61C 13/0003* (2013.01);
(Continued)

(58) Field of Classification Search
CPC .. A61F 2310/00131; A61F 2310/00293; A61F 2310/00407; A61F 2310/00413;
(Continued)

(56) References Cited

U.S. PATENT DOCUMENTS 5,839,900 A * 11/1998 Billet ................. A61C 13/0003
433/218
6,322,728 B1 * 11/2001 Brodkin ............. A61C 13/0003
264/113
(Continued)

FOREIGN PATENT DOCUMENTS

| EP | 1354567 B1 | 10/2003 | |
| WO | WO-2007097747 A1 * | 8/2007 | ......... A61C 13/0019 |
| WO | 2012064620 A1 | 5/2012 | |

OTHER PUBLICATIONS

Saejin Park, Duck H. Wang, Dongsheng Zhang, Elaine Romberg, Dwayne Arola "Mechanical properties of human enamel as a function of age and location in the tooth", J Mater Sci: Mater Med (2008) 19:2317-2324 (Year: 2008).*

(Continued)

*Primary Examiner* — Peter L Vajda
*Assistant Examiner* — S. Behrooz Ghorishi
(74) *Attorney, Agent, or Firm* — W&C IP

(57) ABSTRACT

A method of fabricating a dental restoration is provided that includes the initial step of providing a powder of a dental material. An amount of a binder is then selectively deposited onto the powder of the dental material to produce an unfinished layer of the dental material. Multiple layers of the dental material are then produced by continually providing a powder of dental material and selectively depositing an amount of a binder until a three-dimensional unfinished model is produced. The unfinished model is then separated from an amount of unaffected powder, and is sintered to (Continued)

System overview | Schematics of process produce a three-dimensional dental restoration having a functionally-graded structure.

24 Claims, 27 Drawing Sheets

(51) Int. Cl.

| | | |
|---|---|---|
| B29C 64/165 | (2017.01) | |
| A61K 6/15 | (2020.01) | |
| A61K 6/80 | (2020.01) | |
| A61K 6/813 | (2020.01) | |
| B33Y 10/00 | (2015.01) | |
| B33Y 80/00 | (2015.01) | |
| B28B 1/00 | (2006.01) | |
| B29C 35/08 | (2006.01) | |
| B29L 31/00 | (2006.01) | |

(52) U.S. Cl.
CPC ............ *A61C 13/0004* (2013.01); *A61K 6/15* (2020.01); *A61K 6/80* (2020.01); *A61K 6/813* (2020.01); *B28B 1/001* (2013.01); *B29C 35/08* (2013.01); *B29C 64/165* (2017.08); *B33Y 10/00* (2014.12); *B33Y 80/00* (2014.12); *B29C 2035/0822* (2013.01); *B29C 2035/0827* (2013.01); *B29L 2031/7536* (2013.01)

(58) Field of Classification Search
CPC ........ A61F 2/3099; A61F 2/36; A61F 2/3662; A61F 2/38; A61F 2/3804; A61F 2/3859; A61F 2/40; A61F 2/4225; A61F 2/4241; A61F 2/4261; A61F 2002/30028
See application file for complete search history.

(56) References Cited

U.S. PATENT DOCUMENTS

| 6,955,776 | B1* | 10/2005 | Feenstra | ............ | A61C 13/0004 |
| | | | | | 264/16 |
| 7,666,522 | B2 | 2/2010 | Justin et al. | | |
| 7,951,412 | B2 | 5/2011 | Justin et al. | | |
| 8,491,936 | B2 | 6/2013 | Rabiei et al. | | |
| 2003/0114936 | A1* | 6/2003 | Sherwood | ................. | A61F 2/28 |
| | | | | | 623/23.58 |
| 2008/0206710 | A1 | 8/2008 | Kruth et al. | | |
| 2008/0213727 | A1 | 9/2008 | Zhang et al. | | |
| 2008/0237933 | A1* | 10/2008 | Hochsmann | ............ | B33Y 10/00 |
| | | | | | 264/463 |
| 2010/0143868 | A1 | 6/2010 | Hintersehr | | |
| 2011/0183297 | A1* | 7/2011 | Thiel | ...................... | A61C 13/20 |
| | | | | | 433/217.1 |
| 2012/0148983 | A1 | 6/2012 | Mullen et al. | | |
| 2012/0285019 | A1* | 11/2012 | Schechner | ......... | A61C 13/0004 |
| | | | | | 29/896.1 |
| 2015/0366802 | A1* | 12/2015 | Jacob | ..................... | A61K 31/55 |
| | | | | | 424/465 |

OTHER PUBLICATIONS

Aleš Jíral, Jiří Němeček "Nanoindentation of Human Tooth Dentin", Key Engineering Materials vol. 606 (Mar. 2014) pp. 133-136 (Year: 2014).*
Kuroda D., Niinomi M., Morinaga M., Kato Y., Yashiro T. Design and mechanical properties of new b type titanium alloys for implant materials. Mater Sci Eng A 1998; 243: 244-9.
Niinomi M. Biologically and Mechanically Biocompatible Titanium Alloys. Materials Transactions 2008; 49 (10) 2170-2178.
Guillemot F. Recent advances in the design of titanium alloys for orthopedic applications. Expert Rev Med Devices. 2005; 2: 741-8.
Parr G. Titanium: the mystery metal of implant dentistry. J Prosthet Dent 1985; 54:410-3.
Bhattarai S.R., Khalil K.A., Dewidar M., Hwang P.H., Yi H.K., Kim H.Y. Novel production method and in-vitro cell compatibility of porous Ti—6Al—4V alloy disk for hard tissue engineering. J Biomed Mater Res A. 2008; 86: 289-99.
Krishna B.V., Bose S., Bandyopadhyay A. Low stiffness porous Ti structures for load-bearing implants. Acta Biomater. 2007; 3: 997-1006.
Turner T.M., Sumner D.R., Urban R.M., Rivero D.R., Galante J.O. A comparative study of porous coatings in a weight-bearing total hip-arthroplasty model. J Bone Joint Surg Am 1986; 68: 1396-409.
Head W.C., Bauk D.J., Emerson Jr R.H. Titanium as the material of choice for cementless femoral components in total hip arthroplasty. Clin Orthop Relat Res 1995; 311: 85-90.
Oh I.H., Nomura N., Masahashi N., Hanada S. Mechanical properties of porous titanium compacts prepared by powder sintering. Scripta Mater 2003; 49: 1197-202.
Hollander D.A., Von Walter M., Wirtz T., Sellei R. Structural, mechanical and in vitro characterization of individually structured Ti—6Al—4V produced by direct laser forming. Biomaterials. 2006; 27: 955-63.
Stamp R., Fox P., O'Neill W., Jones E., Sutcliffe C. The development of a scanning strategy for the manufacture of porous biomaterials by selective laser melting. J Mater Sci Mater Med. 2009; 20: 1839-48.
Traini T., Mangano C., Sammons R.L., Mangano F. Direct laser metal sintering as a new approach to fabrication of an isoelastic functionally graded material for manufacture of porous titanium dental implants. Dent Mater. 2008; 24: 1525-33.
Mullen L., Stamp R.C., Brooks W.K., Jones E., Sutcliffe C.J. Selective Laser Melting: a regular unit cell approach for the manufacture of porous, titanium, bone in-growth constructs, suitable for orthopedic applications. J Biomed Mater Res B Appl Biomater. 2009; 89: 325-34.
Santos E.C., Shiomi M., Osakada K., Laoui T. Rapid manufacturing of metal components by laser forming. Int J Mach Tools Manuf 2006; 46: 1459-1468.
Tolochko N.K., Laoui T., Khlopkov Y.V., Mozzharov S.E., Titov V.I., Ignatiev M.B. Absorptance of powder materials suitable for laser sintering. Rapid Prototyping J 2000; 6: 155-160.
Bandyopadhyay A., Espana F., Balla V.K., Bose S. Influence of porosity on mechanical properties and in vivo response of Ti6Al4V implants. Acta Biomater. 2010; 6: 1640-8.
Pilliar R.M. Porous-surfaced metallic implants for orthopaedic applications. J Biomed Mater Res—Appl Biomater 1987, 21: 1-33.
Clemow A.J.T., Weinstein A.M., Klawitter J.J., Koeneman J., Anderson J. Interface mechanics of porous titanium implants. J Biomed Mater Res 1981; 15: 73-82.
Wennerberg A., Albrektsson T. Effects of titanium surface topography on bone integration: a systematic review. Clin Oral Implants Res. 2009; 20: 172-84.
Shalabi M.M., Gortemaker A., Van't Hof M.A., Jansen J.A., Creugers N.H. Implant surface roughness and bone healing: a systematic review. J Dent Res. 2006; 85: 496-500.
Le Guéhennec L., Soueidan A., Layrolle R, Amouriq Y. Surface treatments of titanium dental implants for rapid osseointegration. Dent Mater. 2007; 23: 844-54.
Hodosh M., Povar M., Shklar G. The dental polymer implant concept. J Prosthet Dent 1969: 22: 371-380.
Pirker W., Kocher A. Immediate, non-submerged, root-analogue zirconia implant in single tooth replacement. Int J Oral Maxillofac Surg. 2008; 37: 293-5.
Kohal R.J., Hürzeler M.B., Mota L.F., Klaus G., Caffesse R.G., Strub J.R. Custom—made root analogue titanium implants placed into extraction sockets. Clin Oral Implants Res 1997; 8: 386-392.
Pirker W., Kocher A. Immediate, non-submerged, root-analogue zirconia implants placed into single-rooted extraction sockets: 2-year follow-up of a clinical study. Int J Oral Maxillofac Surg. 2009; 38: 1127-32.
Zhang Y., Chai H., Lawn B.R. Graded Structures for All-ceramic restorations. J Dent Res. 2010; 89(4): 417-421.

(56) References Cited

OTHER PUBLICATIONS

Zhang Y., Chai H., Lawn B.R. Chipping resistance of graded zirconia ceramics for dental crowns. J Dent Res. 2012; 91(3): 311-315.

Baggi L., Cappelloni I., Di Girolamo M., Maceri F., Vairo G. The influence of implant diameter and length on stress distribution of osseointegrated implants related to crestal bone geometry: a three-dimensional finite element analysis. J Prosthet Dent. 2008;100:422-31.

Lee J.S., Cho I.H., Kim Y.S., Heo S.J., Kwon H.B., Lim Y.J. Bone-implant interface with simulated insertion stress around an immediately loaded dental implant in the anterior maxilla: a three-dimensional finite element analysis. Int J Oral Maxillofac Implants. 2012;27:295-302.

Van Noort R. The Future of Dental Devices is Digital. Dental Materials. 2012; 28:3-12.

Atzeni E., Iuliano L., Minetola P., Salmi A. Proposal of an Innovative Benchmark for Accuracy Evaluation of Dental Crown Manufacturing. Computers in Biology and Medicine. 2012; 42:548-555.

Silva N.F.R.A., Witek L., Coelho P.G., Thompson V.P., Rekow E.D., Smay J. Additive CAD/CAM Process for Dental Prostheses. Journal of Prosthodontics. 2011; 20:93-96.

Ebert J., Ozkol E., Zeichner A., Uibel K., Weiss O., Koops U., Telle R., Fischer H. Direct Inkject Printing of Dental Prostheses Made of Zirconia. Journal of Dental Research. 2009; 88(7):673-676.

Conrad H.J., Seong W.J., Pesun I.J. Current ceramic materials and systems with clinical recommendations. J Prosthet Dent, 2007; 98:389-404.

Denry I., Holloway J.A. Ceramics for Dental Applications: A Review. Materials. 3(2010): 351-368.

Rizkalla AS, Jones DW. Mechanical properties of commercial high strength ceramic core materials. Dent Mater. 2004;20:207-12.

Rizkalla AS, Jones DW. Indentation fracture toughness and dynamic elastic moduli for commercial feldspathic dental porcelain materials. Dent Mater. 2004;20:198-206.

Guess P.C., Schultheis S., Bonfante E.A., Coelho P.G., Ferencz J.L., Silva N.R.F.A. All-Ceramic Systems: Laboratory and Clinical Performance. Dental Clinics of North America. 55(2011): 333-352.

Heintze S.D., Rousson V. Survival of Zirconia- and Metal-supported Fixed Dental Prostheses: A Systematic Review. Introductory Journal of Prosthodontics. 6(2010): 493-502.

Raigrodskia. J., Hillstead M.B., Meng G.K., Chung K.H. Survival and Complications of Zirconia-based Fixed Dental Prostheses: A Systematic Review. Journal of Prosthetic Dentistry. 107(2012): 170-177.

Sailer I., Fehér A., Filser F., Gauckler L.J, Luthy H., Hammerle C. H. Five-year clinical results of zirconia frameworks for posterior fixed partial dentures. Introductory Journal of Prosthodontics. 20(2007): 383-388.

Schwarz S., Shroder C., Hassel A., Bomicke W., Rammelsberg P. Survival and Chipping of Zirconia-based and Metal-ceramic Implant-supported Single Crowns. Clinical Implant Dentistry and Related Research. 14(2011): 119-125.

He L., Swain M.W. Enamel—A Functionally graded natural coating. Journal of Dentistry. 37(2009): 596-603.

An B., Wang R., Arola D., Zhang D. The role of property gradients on the mechanical behavior of human enamel. Journal of the Mechanical Behavior of Biomedical Materials. 9(2012): 63-72.

Zhang Y., Kim J. Graded structure for damage resistant and aesthetic all-ceramic restorations. Dental Materials. 25(2009): 781-790.61.

Zhang Y., Ma L. Optimization of ceramic strength using elastic gradients. Acta Materialia. 57(2009): 2721-2729.

Zhang Y. Overview: Damage resistance of graded ceramic restorative materials. Journal of the European Ceramic Society. 32(2012): 2623-2632.

Zhang Y., Sun M-J, Zhang D. Designing functionally graded materials with superior load-bearing properties. Acta Biomaterialia. 8(2012): 1101-1108.

Katz R.N. Advanced ceramic (Dental ceramic). Nov. 21, 2000.

Harlan N., Park, S-M., Bourell D.L., Beaman J.J.. Selective laser sintering of zirconia with micro-scale features. Proceedings of the 10th Solid Freeform Fabrication Symposium, Austin, TX, USA, 1999.

Wang H., Bourell D.L., Beaman J.J. Selective laser sintering of quartz powder. Proceedings of the 8th Solid Freeform Fabrication Symposium, Austin, TX, USA, 1997.

Klocke F., Wirtz, H.. Selective laser sintering of zirconium silicate. Proceedings of the 9th Solid Freeform Fabrication Symposium, Austin, TX, USA, 1998.

Denham H.B., Cesarano J., King B.H. Mechanical behavior of robocast alumina. Proceedings of the 9th Solid Freeform Fabrication Symposium, Austin, TX, USA, 1998.

Dai C., Qi G., Rangarajan S., Wu S., Langrana N.A., Safari A., Danforth S. C. High quality, fully dense ceramic components manufactured using fused deposition of ceramics (FDC). Proceedings of the 8th Solid Freeform Fabrication Symposium, Austin, TX, USA, 1997.

Levy R.A., Chu T-M.G., Halloran J.W., Feinberg S.E, Hollister S. CT-generated porous hydroxyapatite orbital floor prosthesis as a prototype bioimplant. American Journal of Neuroradiology. 18(1997): 1522-1525.

Cima M.J., Oliveira M., Wang H.R., Sachs E., Holman R. Slurry-based 3DP and fine ceramic components. Proceedings of the 12th Solid Freeform Fabrication Symposium, Austin, TX, USA, 2001.

Uhland S, Holman R, Debear B, Saxton P, Cima M, Sachs E. Three-dimensional printing, 3DP, of electronic ceramic components. Proceedings of the 10th Solid Freeform Fabrication Symposium, Austin, TX, USA, 1999.

Yang L., Zhang S., Oliveira G., Stucker B. Development of a 3D printing method for production of dental application. Proceedings of the 24th Solid Freeform Fabrication Symposium, Austin, TX, USA, 2013.

Jackson T.R., Liu H., Patrikalakis N.M., Sachs E.M., Cima M.J. Modeling and designing functionally graded material components for fabrication with local composition control. Materials and Design. 20(1999): 63-75.

Noecker F.F., Dupont J.N. Functionally Graded Copper—Steel Using Laser Engineered Net Shaping Process. Proceedings of the 13th Solid Freeform Fabrication Symposium, Austin, TX, USA, 2002.

Gasdaska C., Clancy R., Ortiz M., Jamalabad V., Virkar A., Popovitch D. Functionally Optimized Ceramic Structures. Proceedings of the 9th Solid Freeform Fabrication Symposium, Austin, TX, USA, 1998.

Jafari M.A., Han W., Mohammadi F., Safari A., Danforth S.C., Langrana N. A novel system for fused deposition of advanced multiple ceramics. Rapid Prototyping Journal. 692000): 161-174.

He L., Yin Z., Van Vuuren L.J., Carter E.A., Liang, X. A natural functionally graded biocomposite coating-human enamel. Acta Biomaterialia. 9(5), 2013: 6330-6337.

Jones D.W., "Development of dental ceramics: an historical prospective", Dent Clin N 29: 621-644.

Barreiro M.M, Riesgo O., Vicente E. E, "Phase identification in dental porcelains for ceramo-metallic restorations", Dent Mater 5: 51-7.

Burke F.J., Lucarotti P.S., "Ten-year outcome of crowns placed within the General Dental Services in England and Wales", J Dent 37:12-24.

Rekow E.D., Silva N.R.F.A., Coelho P.G., Zhang Y., Guess P., Thompson V.P., "Performance of dental ceramics: challenges for improvements", J Dent Res 90:937-952.

Pjetursson B.E., Sailer I., Zwahlen M., Hammerle C.H., "A systemic review of the survival and complication rates of all-ceramic and metal-ceramic reconstructions", J Dent Reg 90:938-986.

Valenti M., Valenti A, "Retrospective survival analysis of 261 lithium disilicate crowns in a private general practice", Quintessence Int 40: 573-579.

Whittneben J.G., Write R.F., Weber H.P., Gallucci G.O., "A systematic review of the clinical performance of CAD/CAM single-tooth restorations", Int J Prosthodont 22:466-471.

(56) References Cited

OTHER PUBLICATIONS

Zhang S., Yang L., Zandinejad A., Miyanaji H., Stucker B., An experimental study of ceramic dental porcelain materials using a 3D print (3DP) process. Proceeding of Solid Freeform Fabrication (SFF) Symposium, 2014.

Gonzaga C.C., Yoshimura H.N., Cesar P.F., Miranda JR W.G., "Subcritical crack growth in porcelains, glass-ceramics, and glass-infiltrated alumina composite for dental restorations", J Mater Sci Mater Med 20: 1017-24.

Fairhurst C.W., Lockwood P.E., Ringle R.D., Twiggs S.W.' "Dynamic fatigue of feldspathic porcelain", Dent Mater 9: 269-73.

Yoshimura H.N., Cesar P.F., Miranda W.G., Gonzaga C.C., Okada C.V., Goldenstein H., "Fracture toughness of dental porcelains evaluated by IF, SCF, and SEPB methods", Am Ceram Soc 88: 1680-3.

Li J., Liao H., Hermansson L. Sintering of partially-stabilized zirconia and partially-stabilized zirconia-hydroxyapatite composites by hot isostatic pressing and pressureless sintering, Biomaterials, 17 (1996), 1787-1790.

Itoh H., Wakisaka Y., Ohnuma Y., Kuboki Y. A new porous hydroxyapatite ceramic prepared by cold isostatic pressing and sintering synthesized flaky powder. Dental Materials Journal, 13 (1994), 25-35.

Denry I. and Kelly R., State of the art of zirconia for dental applications. Dental Materials, 24 (2008), 299-307.

Martorelli M., Gerbino S., Giudice M., Ausiello P. A comparison between customized clear and removable orthodontic appliances manufactured using RP and CNC techniques, 29 (2013), e1-e10.

Mohanty S., Rameshbabu A.P., Dhara S., Net shape forming of green alumina via CNC machining using diamond embedded tool. 39 (2013), 8985-8993.

Wu M., Tinschert J., Augthun M., Wagner I., Schädlich-Stubenrauch J., Sahm P.R., Spiekermann H. Application of laser measuring, numerical simulation and rapid prototyping to titanium dental castings. Dental Materials, 17 (2001), 102-108.

Azari A., Nikzad S., The evolution of rapid prototyping in dentistry: a review. Rapid Prototyping Journal, 15 (2009), 216-225.

Wang J., Shaw L., Cameron T. Solid Freeform Fabrication of permanent dental restorations via slurry micro-extrusion. Journal of the American Ceramic Society, 89 (2006), 346-349.

Khalyfa A., Vogt S., Weisser J., Grimm G., Rechtenbach A., Meyer W., Schnabelrauch M. Development of a new calcium phosphate powder-binder system for the 3D printing of patient specific implants. 18(2007), 909-916.

Lam C.X.F., Moa X.M, Teoha S.H., Hutmacher D.W. Scaffold development using 3D printing with a starch-based polymer. 20 (2002), 49-56.

Scientific documentation IPS InLine system, 2010.

Aerosil R 972 Hydrophobic fumed silica MSDS.

Spierings A.B., Schneider M. Comparison of density measurement techniques for additive manufactured metallic parts. Rapid Prototyping Journal, 17(5), 2011, 380-386.

Giannakopoulos AE, et al. Development of strong surfaces using functionally graded composites inspired by natural teeth. Journal of engineering materials and technology, 2010 132(1).

* cited by examiner

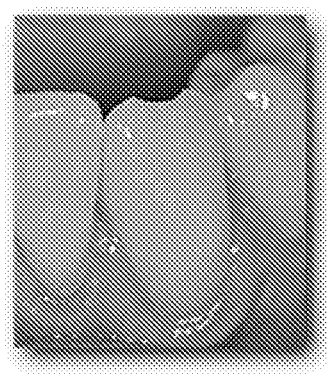
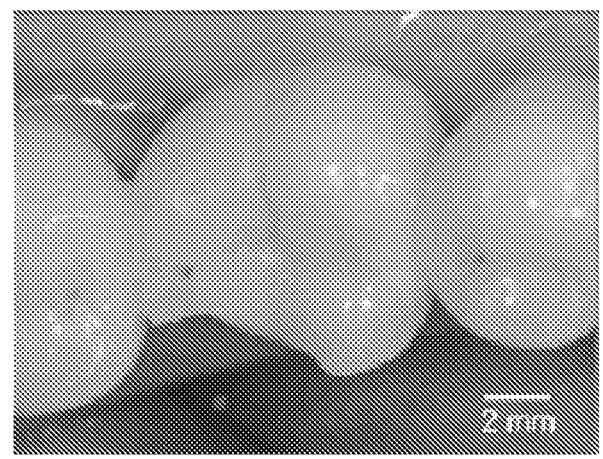
FIG. 15            FIG. 16
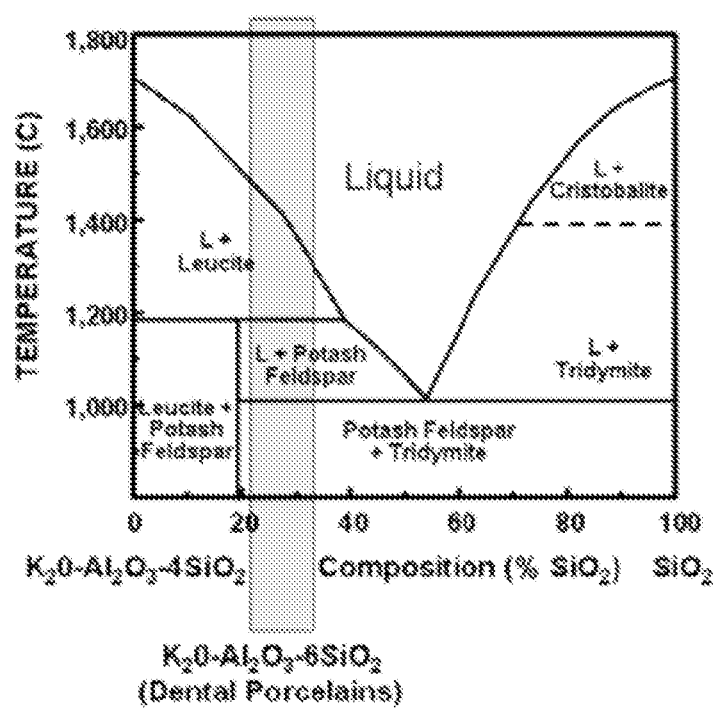
FIG. 17

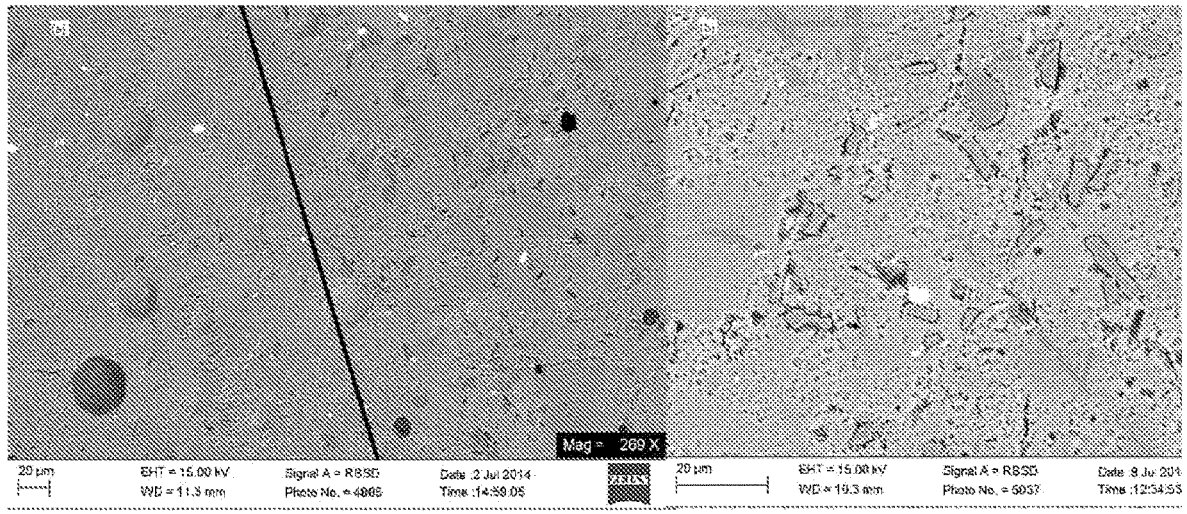
FIG. 22A  FIG. 22B
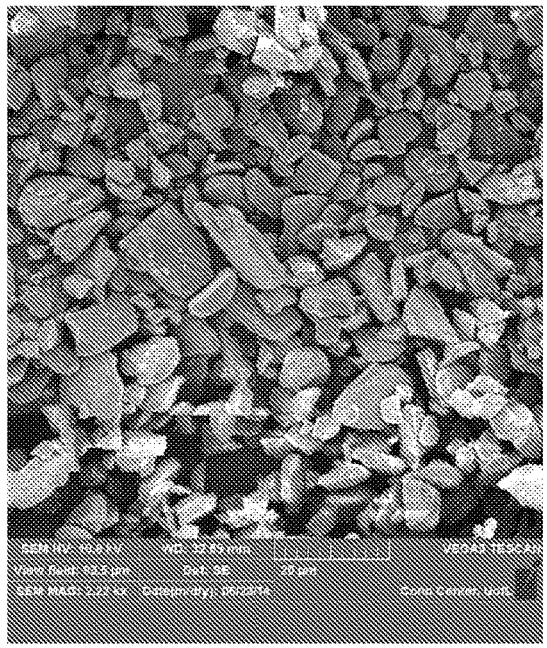
FIG. 23

METHODS FOR FABRICATING DENTAL RESTORATIONS

RELATED APPLICATIONS

This application claims priority from U.S. Provisional Application Ser. No. 61/987,643, filed May 2, 2014, the entire disclosure of which is incorporated herein by this reference.

TECHNICAL FIELD

The presently-disclosed subject matter relates to methods for fabricating dental restorations. In particular, the presently-disclosed subject matter relates to methods for fabricating dental restorations, such as dental crowns, whereby a binder is selectively deposited onto a powder of a dental material to produce a three-dimensional model which, after sintering, produces a three-dimensional dental restoration having a desired physical geometry and one or more functionally-graded mechanical properties.

BACKGROUND

Due to the increasing demand for improved aesthetics, ceramic materials have been used more widely in various dental applications such as veneers, inlays, onlays, crowns, bridges (fixed dental restorations), and other dental restorations. In addition to increased translucency, ceramics possess good biocompatibility, and, in general, exhibit good abrasive resistivity, which makes ceramics attractive as dental materials. However, when ceramics were first introduced into dentistry, the relatively low mechanical strength of the ceramic materials was a common problem.

Ceramics and glasses are brittle in that those materials display a high compressive strength, but also display a low tensile strength and may fracture under very low strain (0.1%, 0.2%). In this regard, dental ceramics are commonly viewed as having a number of disadvantages when used as restorative materials (mostly due to their inability to withstand functional forces that are present in the oral cavity). Consequently, dental ceramics were not initially utilized in the premolar and molar areas. Further material development has enabled the use of ceramics in posterior restorations, as well as in structures over dental implants. Nevertheless, all dental ceramics still generally display low fracture toughness when compared with other dental materials such as metal-ceramic or specialty solo metals. Indeed, zirconia-based ceramics have been considered the strongest of all ceramic restorations available in the market. However, it was previously reported that the catastrophic failure rate within the zirconia core ceramic was around 7% for single crowns after 2 years, and 1% to 8% for fixed dental prostheses after 2-5 years. One major cause of that catastrophic failure was occlusal overload due to bruxism, which causes cracks at the cementation surface. Those cracks then propagate towards the surface, and eventually cause the entire restoration to fracture. In fact, in general, the survival rate for metal-ceramic restorations was ultimately found to be significantly higher than zirconia-based or any other ceramic restorations.

In addition to the problems inherent in a number of dental materials, in recent years, it has also been discovered that human dental structures are in fact structures with graded properties. The enamel of the tooth has an elastic modulus of about 80 GPa and hardness of about 4 GPa, while the dentin of the tooth has an elastic modulus of about 20 GPa and a hardness of about 1 GPa. Furthermore, even within the enamel itself, there exists a gradual change of mechanical properties from the inner region to the outer surface, which is largely influenced by a change of microstructure. It has also been found that upon loading, more energy is dissipated through the inner enamel, which undergoes viscoelastic deformation over a relatively large area, and thus the tooth may accommodate higher levels of strain. By comparison, most ceramic dental restoration parts have relatively homogenous mechanical properties throughout the structure. Therefore, the cores of the dental restorations often have significantly higher stiffness than that of the human dentin, making them less capable of absorbing strain and other forces applied to it.

Despite the recognition of graded properties in dental structures, such as enamel, it is almost impossible to create a dental part with a graded elastic modulus with currently known processes. The currently known sintering, casting, or milling processes are all incapable of producing controlled inhomogeneity, and machining processes can only produce external features. Some previous works have shown that the use of dental restorations with a non-uniform elastic modulus could significantly increase the mechanical performance of the zirconia parts. In particular, in one series of works, it was observed that fabricated graded structures could be produced using silica-alumina with a low elastic modulus and using zirconia with a high elastic modulus. By infiltrating glass into zirconia plates at both ends of the part, glass-ceramic-glass graded structures were created with relatively soft skins and stiff cores. Those results also showed a significant increase (20%-50%) in the fracture loads of the infiltrated material. Nevertheless, the ability to mimic the structure of a natural tooth and produce a graded elastic modulus was still limited in those studies.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods for fabricating dental restorations. In particular, the presently-disclosed subject matter includes methods for fabricating dental restorations, such as dental crowns, whereby a binder is selectively deposited onto a powder of a dental material to produce a three-dimensional model which, after sintering, produces a three-dimensional dental restoration having a desired physical geometry and one or more functionally-graded mechanical properties.

In some implementations of the presently-disclosed subject matter, a method of fabricating a dental restoration is provided that includes the initial step of providing a powder of a dental material, such as, in some implementations, a ceramic (e.g., porcelain) powder. Such a layer of powdered dental material is, in certain implementations, deployed via a powder deploy mechanism. For instance, in some implementations, the powder deploy mechanism is a rotating roller, that, in certain implementations, can be used to vary the amount of powder of the dental material that is being provided to produce a layer of dental material having a portion with an elasticity, hardness, or porosity different than that of an adjacent portion.

Regardless of the particular mechanism used to provide the powder of dental material, once the dental material powder is provided, an amount of a binder is then selectively deposited onto the powder of the dental material to produce an unfinished layer of the dental material. Similar to the provision of the powder of dental material, the binder can also be selectively deposited onto the powder of the dental material by varying the amount of binder deposited onto the powder in order to produce a layer of dental material having a portion with an elasticity, hardness, or porosity different than that of an adjacent portion. In some implementations, the binder includes one or more organic compositions, inorganic compositions, surfactants, dispersants, and combinations thereof. In some implementations that make use of inorganic compositions in the binder (e.g., iron oxide particles) varying the amount of inorganic compositions included in the binder can also be used to produce a layer of dental material having a portion with an elasticity, hardness, or porosity different than that of an adjacent portion. Such a selective deposition of a binder is, in some implementations, performed by an inkjet printing platform. In some implementations, the amount of the binder selectively deposited onto the powder of dental material is sufficient to produce a binder saturation level of about 45% to about 75%.

Upon depositing the binder onto the powder of dental material, the binder is then optionally cured by, for example, subjecting the binder to thermal radiation, ultraviolet radiation, or both. In this regard, in some implementations, the time period used to cure the binder is also varied to produce a layer of dental material having a portion with an elasticity, hardness, or porosity different than that of an adjacent portion. However, irrespective of whether the binder is cured following its deposition, the steps of providing a powder of dental material and selectively depositing a binder on the powder of dental material is then repeated multiple times to produce a three-dimensional unfinished model in a layerwise fashion. In some implementations, the production of a three-dimensional model is done by repeating the steps of providing a powder of dental material and selectively depositing a binder about 10 to about 1,000 times.

Subsequent to producing the unfinished model, the unfinished model is then separated from any amount of unaffected (i.e., unbound) powder and the unfinished model is sintered to produce a three-dimensional dental restoration having a functionally-graded structure. In some implementations, the sintering step is performed by heating the unfinished model to a temperature of about 750° C. to about 950° C. In other implementations, the sintering is performed by heating the unfinished model in a stepwise fashion to a first temperature of about 500° C. for a first predetermined time period, and then to a second temperature of about 750° C. to about 950° C. for a second predetermined time period. In some implementations, the first predetermined time period is about 30 min and the second predetermined time period is about 1 min to about 9 hrs or more.

With respect to the functionally-graded three-dimensional dental restoration produced by making use of the foregoing steps, in some implementations, the steps are configured to produce a dental restoration having an outer enamel-like portion and an inner dentin-like portion, where the outer enamel-like portion further includes an outer layer and an inner layer. In some implementations, the outer enamel-like portion produced in accordance with the presently-disclosed methods has a width that extends from the outer layer to the inner layer, and further has a hardness and an elastic modulus that reduces across the width of the enamel-like portion from the outer layer to the inner layer. For instance, in some implementations, the outer layer of the enamel-like portion is produced such that it has an elastic modulus of about 100 GPa to about 140 GPa and a hardness of about 0.8 GPa to about 1.2 GPa, while the inner layer of the enamel like-portion is produced such that it has an elastic modulus of about 40 GPa to about 80 GPa and a hardness of about 0.4 GPa to about 0.8 GPa. In this regard, in some implementations, the dentin-like portion included in such a functionally-graded three-dimensional dental restoration can be produced to have an elastic modulus of about 15 GPa to about 45 GPa.

Further features and advantages of the present invention will become evident to those of ordinary skill in the art after a study of the description, figures, and non-limiting examples in this document.

BRIEF DESCRIPTION OF THE DRAWINGS

FIG. 15 is an image showing a chipping failure in a porcelain dental restoration.

FIG. 16 is an image showing a bulk fracture in a porcelain dental restoration.

FIG. 17 is a phase diagram of typical dental porcelains.

FIGS. 22A-22B include images of micrographs of a graded structure (FIG. 22A) and a 5% alumina porcelain structure (FIG. 22B) produced in accordance with the presently-disclosed subject matter.

FIG. 23 is a scanning electron microscope (SEM) image showing the morphology of alumina powder.

(FIG. 43A) and 900° C. (FIG. 43B).

DESCRIPTION OF EXEMPLARY EMBODIMENTS

Figure 1:
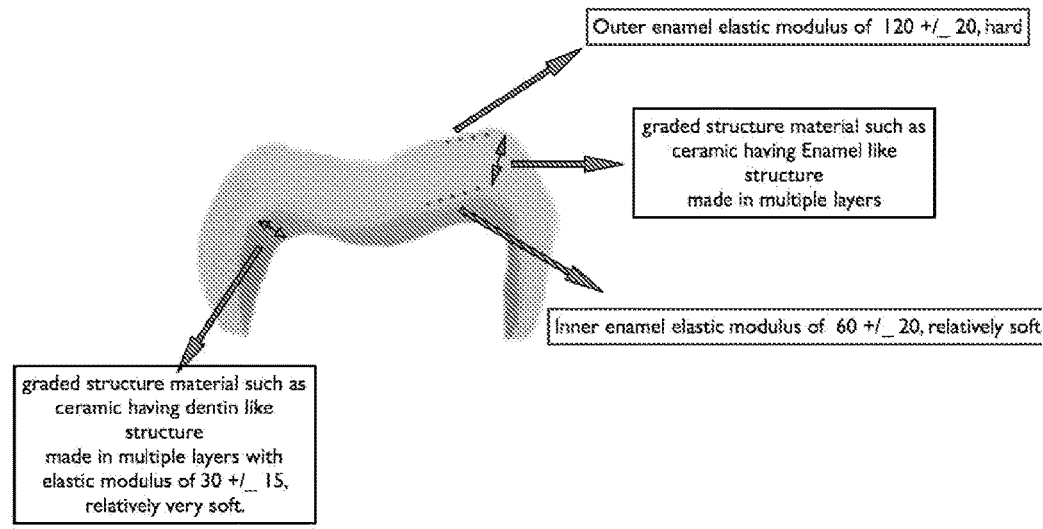
FIG. 1 is a schematic diagram showing a cross section of a full contour dental crown made in accordance with the presently-disclosed subject matter.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a restoration" includes a plurality of such restorations, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes methods for fabricating dental restorations and, more particularly, methods of fabricating dental restorations, such as crowns, whereby a powder of a dental material is provided and a binder is selectively deposited onto the powder of a dental material to produce an unfinished layer of the dental material. That process of providing a powder of a dental material and selectively depositing the binder is then repeated a number of times to thereby produce a three-dimensional unfinished model. The three-dimensional unfinished model is then sintered to produce a functionally-graded structure. In some embodiments, the methods of the present invention advantageously allow the physical geometry and the mechanical properties of a dental restoration to be customized so as to provide a dental restoration, such as a crown, with a physical geometry and mechanical properties that are identical or substantially similar to those found in a naturally-occurring tooth.

In some implementations of the presently-disclosed subject matter, the above-described steps are performed and the dental restorations are produced by making use of an additive manufacturing process, such as a three-dimensional (3D) printing process. It is, of course, appreciated that certain additive manufacturing fabricates parts by discretizing digital 3D virtual models into layers and then building the parts layer-by-layer. Indeed, various additive manufacturing processes have proven capable of producing ceramic freeform fabrication structures using various materials such as $ZrO_2$, $SiO_2$, $Si_3N_4$, $Al_2O_3$, hydroxyapatite, and $ZrSiO_4$. Among these additive manufacturing processes, it has been found that the 3D printing process is suitable for producing structures with fine feature details and high geometrical accuracies. In a 3D print process, the build material is supplied in powder form and deployed layer-by-layer as the fabrication progresses. A binder-jet system then selectively applies binder on the processed layer to form the desired geometry. Since binders usually have limited strength, the unfinished models then undergo a secondary process, such as sintering, to obtain the final strength. Typically, the 3D printing process uses very fine powder (approximately 0.1-10 μm) and a small sized binder-jet nozzle system (approximately 5-10 μm), and the 3D printing process therefore typically possesses the necessary accuracy and resolution required for dental applications.

By making use of 3D printing processes, in some implementations, the functionally-graded structures can be designed at various scales, including micro- (e.g. material, microstructure), meso- (e.g. composition, interface), and macro- (e.g. topological geometries) scale designs. In some implementations, for ceramic materials, the graded functional design focuses on micro- and meso-scale designs, as the crack susceptibility of ceramics largely prevents the effective use of a macro-scale graded functional design.

In some implementations of the presently-disclosed subject matter, a method of fabricating a dental restoration, such as a ceramic dental crown, is thus provided that makes use of a 3D printing process to produce a dental restoration that mimics the properties of human enamel and dentin and that has a controlled internal porosity. In some implementations, the methods of the presently-disclosed subject matter produce a dental structure having controlled mechanical properties, including, but not limited to, properties such as stiffness, strength, toughness, and service life.

In one exemplary implementation of the presently-disclosed methods, a powder of a dental material is first provided via a powder deploy mechanism, such as a rotating roller, where the deploying speed and the rolling speed are independently controlled and changeable for individual layers. Once the powder of dental material has been sufficiently deposited, a binder is then selectively deposited onto the powder of the dental material to produce an unfinished layer of the dental material. In particular, to selectively deposit the binder, an inkjet printing platform is typically used and moves in a plane parallel to the powder surface and deposits the liquid binder onto the powder surface. In this regard, the deposition of the binder is controlled in such a way that only desired regions of the powder surface are deposited with binder. In some implementations, the amount of binder deposited to each location of the powder bed may be controlled independently as well.

After the inkjet printing platform finishes depositing binder onto the current layer, the powder bed is optionally subjected to thermal or ultraviolet irradiation for a predetermined amount of time to partially or completely cure the binder. After the curing, the entire powder bed is lowered by one layer thickness. An additional layer of powder of dental material is then provided on the previously produced unfinished layer of the dental material, with the thickness of the additional layer of powder being typically fixed even though the thickness can also be readily changed during the deposition process. That process then repeats until all the layers are completed and a three-dimensional unfinished model is produced. The completed, but unfinished, model is then cleaned and separated from the unaffected powder. The unfinished model is then placed into a furnace and sintered at an elevated temperature in various atmospheres to increase the density of the model and finish the dental restoration. In some implementations, the unfinished model obtains the desired mechanical properties and geometrical dimensions after the sintering step to thereby produce a three-dimensional dental crown having a functionally-graded structure. In some implementations, the multiple layers are sintered concurrently with the printing process, while, in other implementations, the entirety of the completed dental crown model is sintered to fuse all of the layers simultaneously. Of course, various techniques and equipment can be used to fully sinter the printed dental restorations (e.g., crowns).

With respect to the powders of dental material, various powders known to those of ordinary skill in the art for use in making dental restorations can be used in accordance with the presently-disclosed subject matter. Such powders include, but are not limited to, ceramic powders such as powdered pure porcelain or its equivalent, as well as porcelain powder combined with other materials such as $ZrO_2$, $SiO_2$, $Si_3N_4$, $Al_2O_3$, hydroxyapatite, lithium disiliacet, and $ZrSiO_4$.

With respect to the binder used in accordance with the methods of the presently-disclosed subject matter, in some implementations, the amount of liquid binder deposited onto each layer is controlled. For example, in one implementation, selected regions in the first layer have an initial amount of binder deposited on the dental material, while other regions in each consecutive layer receive an additional 0.1% liquid binder deposited on them. As a result, the $100^{th}$ layer will thus receive 10% more binder than the first layer. As another example, in some implementations, the amount of liquid binder deposited within the same layer is controlled. In this regard, in those implementations, the exterior boundaries may, for instance, receive 10% more binder compared to other regions. Of course, in yet other implementations, other binder deposition scenarios can also be used that result in different concentrations of binder chemicals at different locations in the finished dental restoration (e.g., crown). By making use of these different types of binder depositions, during the subsequent sintering step, localized and graded mechanical properties can then be achieved through the presence of different concentration of binders. While not wishing to be bound by any particular theory, it is believed that the underlying mechanisms responsible for such localized and graded mechanical properties can include, but are not limited to, porosity generation, initial density gradient via capillary force, and/or residual concentration. In some implementations, to produce a dental restoration having sufficient porosity, strength and other mechanical properties, the amount of binder selectively deposited onto the powder of dental material is sufficient to produce a binder saturation level of about 35%, about 40%, about 45%, about 50%, about 55%, about 60%, about 65%, about 70%, about 75%, about 85%, or about 90%. In some implementations, the binder saturation level is about 45% to about 75% to thereby control the porosity, strength and other mechanical properties of the resulting dental restoration. In other implementations, the mechanical properties of the resulting dental restoration can also be controlled by adjusting the powder deployment parameters (e.g., deployment speed, roller speed) and/or the curing time.

With respect to the layers of dental materials that are deposited in accordance with the presently-disclosed methods, it is contemplated that the number of layers could range from about 10 to about 1,000 depending on the particle size of the dental materials selected and the particular dental restoration being produced. In some implementations, the powders of ceramic dental materials are provided as the manufacturing materials. Additional materials may also be provided to facilitate the process and the property control of the dental materials, such as ceramic materials. For instance, in some implementations, a custom liquid binder is prepared, which may contain organic compositions, inorganic compositions, surfactants, and dispersants. In some implementations, the organic compositions can be used to cross-link the materials under thermal or ultraviolet irradiations, and the inorganic compositions can be used to facilitate the crosslinking process of the organic compositions. In other implementations, the inorganic compositions facilitate the control of the properties of the ceramic materials. Then, in some implementations, the surfactants and dispersants are added as needed to ensure stabilization and homogenous composition of the liquid binder.

In other exemplary implementations of the presently-disclosed subject matter, one or more types of inorganic chemicals can also be added into the binder liquid to produce a homogenous phase. In some implementations, the inorganic chemicals are provided as a particulate, while, in other implementations, the inorganic chemicals are provided in other forms. The liquid phase of the resulting binder liquid may be a suspension with proper surface tension, viscosity, and pH values suitable for the manufacturing platform. Such binders are then deposited on the powder with different local deposition amounts according to the methods discussed above. The completed unfinished model will thus have different concentrations of the inorganic chemicals at different interior locations. During the sintering step, the inorganic chemicals can then be used to alter the effect of sintering and achieve graded mechanical properties in the ceramic structures. In this regard, while not wishing to be held to any particular theory, it is believed that the graded mechanical properties due to inclusion of one or more inorganic chemicals may be caused by mechanisms, including, but not limited to, grain growth inhibition, formation of liquid phase sintering at lower temperatures, exothermal reaction reinforced sintering, and diffusion.

With further respect to the use of various compositions and chemicals in accordance with the presently-disclosed subject matter, in one exemplary implementation, iron oxide ($Fe_3O_4$) particles may be added to an organic binder with zirconia to form a suspension liquid. In such an implementation, during manufacturing, the exterior boundary regions can receive 50% more binder and therefore 50% more iron oxide particles. After the sintering the unfinished model at 1150° C., the finished zirconia dental crown then has a dense shell with coarse zirconia grains (higher hardness) and a more porous core with fine zirconia grains (lower hardness).

Turning now to the sintering of the unfinished models produced in accordance with the presently-disclosed subject matter in order to produce a 3D dental restoration having a functionally-graded structure, in some implementations, the sintering can occur in a single step where an unfinished dental restoration model is heated to a temperature of about 700° C., about 750° C., about 800° C., about 850° C., about 900° C., about 950° C., or about 1000° C. In some implementations, for example, the unfinished model is heated to a temperature of about 750° C. to about 950° C. In other implementations, the sintering or heating of the unfinished model can occur in a step wise fashion. For instance, in such implementations, the sintering comprises heating the unfinished model to a temperature of about 500° C. for a first predetermined time period (e.g., a time period sufficient to burn off the amount of binder present in the unfinished model), and then subsequently heating the unfinished model to a temperature of about 750° C. to about 900° C. for a second predetermined time period. In some implementations, the first predetermined time period is 30 min or less, while the second predetermined time period ranges from 1 min to about 9 hrs to produce a functionally-graded dental restoration.

With reference to FIG. 1, in certain implementations of the presently-disclosed subject matter, an all ceramic dental restoration, such as a full contour crown, is fabricated using the above-described methods such that the dental crown has characteristics which are identical or substantially similar to natural tooth structures (e.g. enamel and dentin). Specifically, in some implementations, by making use of the above-described procedures, the dental crown is designed and fabricated to have an outer hard surface with an elastic modulus of about 120+/−20 GPa and a hardness of about 1.0+/−0.2 GPa. From this hard outer layer, the fabrication of crown can then continue by adding layer by layer, with each layer having a slightly reduced elastic modulus and hardness. In some implementations, the final layer forming the inner surface will have an elastic modulus of about 60+/−20 GPa and a hardness of about 0.6+/−0.2 GPa. In some implementations, the dental crown is designed to replace a portion of dentin in the tooth, and, in these implementations, the inner surface property is reduced even more to match the existing dentin such as having an elastic modulus of about 30+/−15 GPa.

In certain implementations of the presently-disclosed subject matter, the graded mechanical properties can also be pre-determined by designing a 3D virtual geometry with material information. In such implementations, the mechanical specifications can first be provided via finite element analysis, historical data, or experimentation. In some exemplary implementations, multiple mechanical specifications at multiple directions may be required for the ceramic dental prostheses. A mathematical model of the designed structures with graded mechanical properties may be developed, and optimization may be performed in order to achieve the optimized combination of properties. The resulted design of the functionally-graded structure can then be manufactured via the methods described herein above.

In some implementations, a structural crown or other ceramic restoration can also be printed based on the expected location in which the restoration is to be placed in the mouth of a subject (e.g., anterior or posterior) and the amount of expected bite force in that particular location. In some implementations, such restorations can be comprised of, for example, a first flexible layer having 10% to 20% porosity (e.g., by including 10% to 20% percent alumina) and then gradually transition to a last pure ceramic layer having no porosity.

In some implementations, a custom dental restoration can be produced that not only has mechanical properties that mimic those found in the anatomical structures of a natural human tooth, but that also has a color and translucency that mimics those found in the teeth of a particular subject. Using the aforementioned technique allows for the introduction of different shades with different degrees of translucency during the fabrication process. Ceramic or glass powders used in the system have different shades and translucency, and can be applied during the process to fabricate a crown or any other dental restorations having a customized internal shade map that duplicates the teeth of a particular subject.

The presently-disclosed subject matter is further illustrated by the following specific but non-limiting examples.

EXAMPLES

Example 1—Initial Fabrication of a Dental Crown

Figure 2:
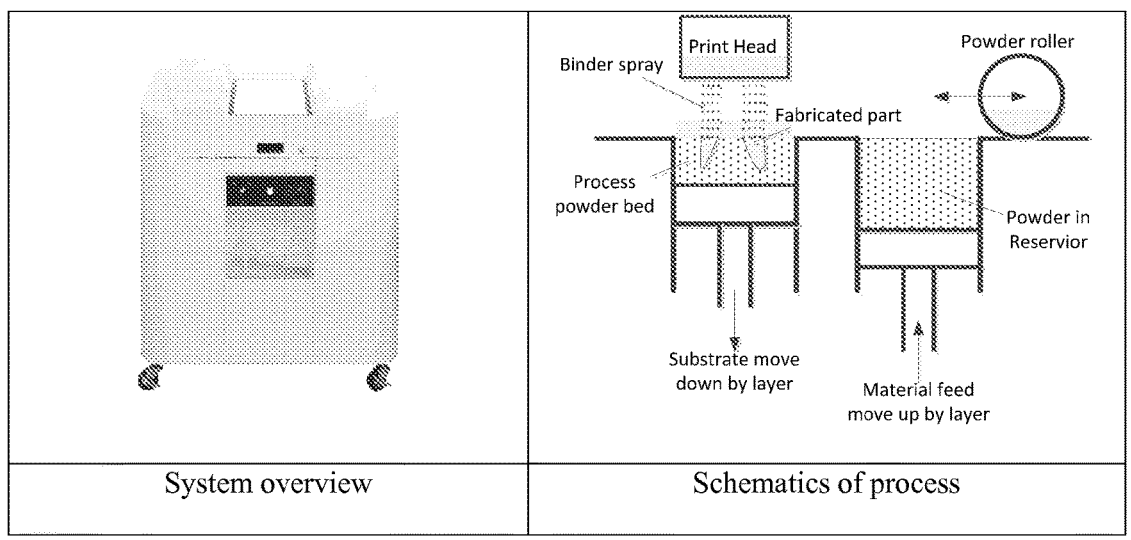
FIG. 2 includes an image and a schematic diagram showing an overview of a printing system used in accordance with the presently-disclosed methods.
Figure 3:
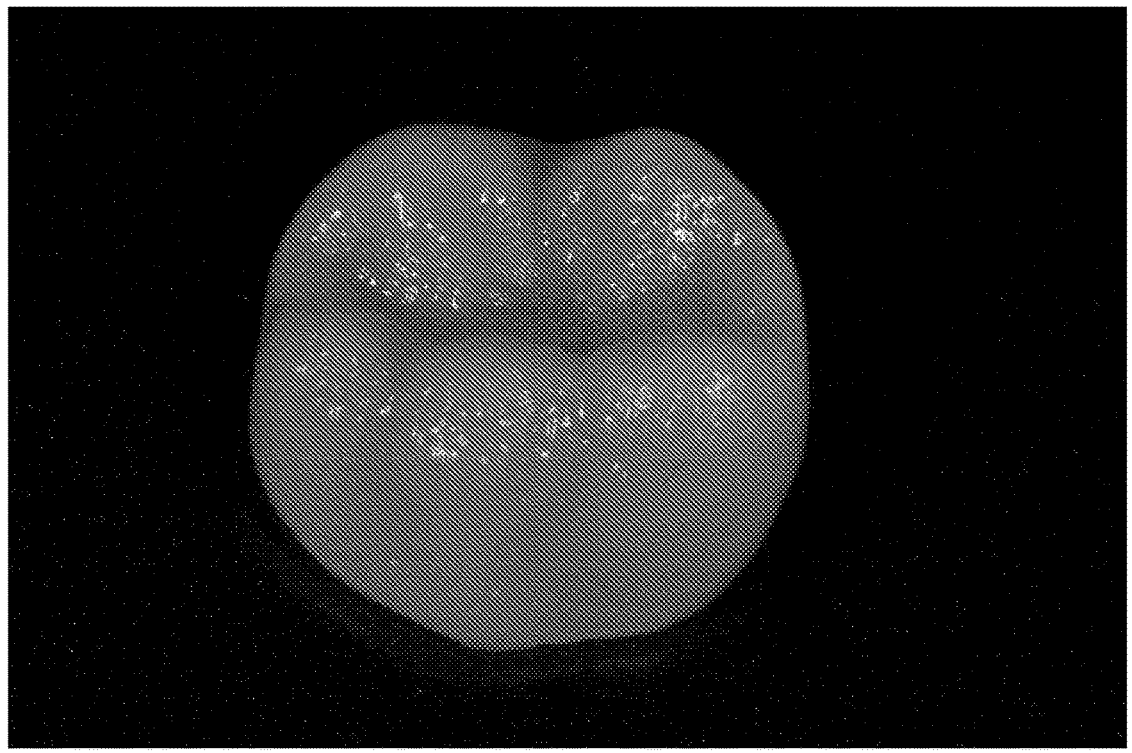
FIG. 3 is an image of a dental restoration made in accordance with the presently-disclosed methods and having desired mechanical properties and geometries.

Dental crown computer-aided design (CAD) models were initial printed with the ExOne® 3D print system manufactured and distributed by The Ex One Company, LLC of North Huntingdon, Pa. FIG. 2 shows an overview of the printing system as well as the schematics of the printing process. The dental ceramic materials were stored in the material reservoir, and deployed layer by layer onto the process platform via a powder roller. A print head selectively sprayed "ink" in the form of a binder onto the powder bed, which served to bind the powder and form the desired geometry. The selective printing and binding steps continued layer by layer until the entire geometry was generated. After the unfinished model was fabricated, the unfinished model underwent a drying step in order to fully cure the binder, followed by a final sintering step to densify the model and achieve the final desired mechanical property and geometry (see FIG. 3). During the printing process, the binder deposition could be adjusted at individual locations, therefore enabling selective binder control of the unfinished model. By combining binder control with sintering control, graded material composition and mechanical properties could be controlled, thus enabling the advanced design and fabrication of specific dental ceramic structures.

Figure 4:
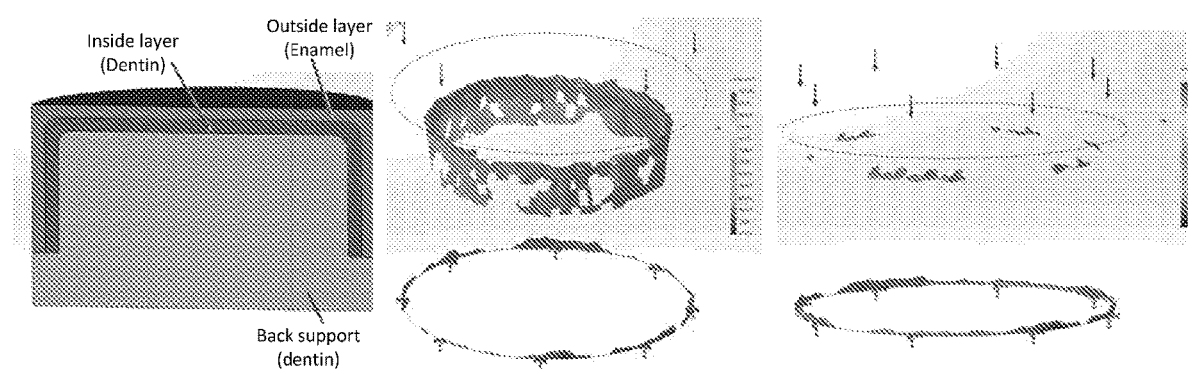
FIG. 4 includes a schematic diagram and stress distribution models for a dental restoration made in accordance with the presently-disclosed methods.

In particular, by making use of the printing methodology, a laminated gradient could be introduced into the dental structures, with high stiffness laminates at the outside surface and low stiffness laminates at the inside surface (see, e.g., schematics of graded structure in FIG. 4A). Analysis of such a model showed significant improvement of stress distribution when graded structures were present, (see FIG. 4B and FIG. 4C). Improved stress distribution indicated better load bearing capability and smaller overall structure damage over time, which, without wishing to be bound by any particular theory, was believed to be directly related to the service life of the dental crown.

Subsequent to the printing of the initial model, to perform an initial evaluation of the dental restorations produced by the presently-described methods, the material property data shown in Table 1 was first used. The Poisson's ratio values were obtained from literature sources, while the elastic modulus values were pre-defined and the shear modulus was determined by assuming $G=E/3$.

TABLE 1

Mechanical properties of dental simulation materials.

| Material | Modulus (GPa) | Poisson's ratio | Shear modulus (GPa) |
|---|---|---|---|
| Dentin | 19 | 0.31 | 0.6 |
| Enamel | 90 | 0.3 | 30 |

Figure 5:
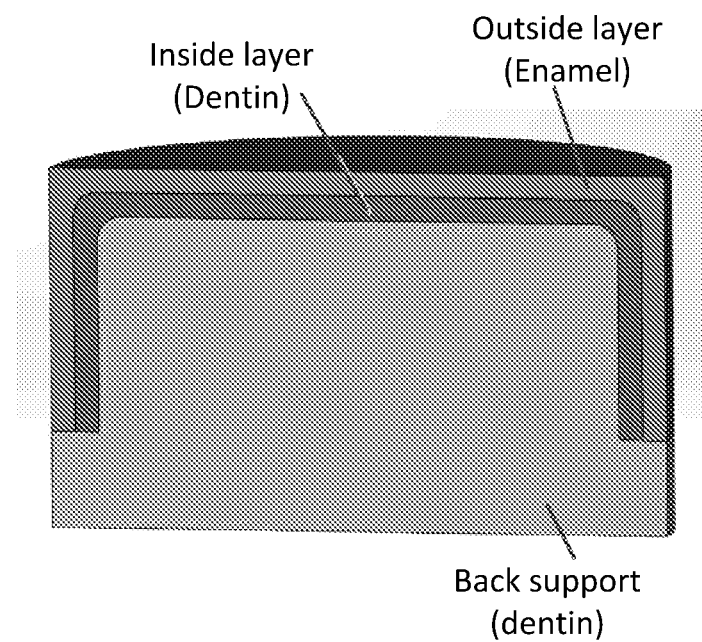
FIG. 5 is a simplified schematic diagram of a dental crown prosthesis made in accordance with the presently-disclosed methods.

With those parameters in mind, a simplified model of the dental crown prosthesis made according the methods of the present invention was developed, as shown in FIG. 5. Briefly, in the model, the outside layer simulated enamel, while the inside layer simulated dentin. The thickness of each layer was 0.5 mm, and the overall dimension of the cylindrical crown was φ13 mm×5 mm. The material for the back support was defined as dentin. Two examples of material combination for crown prosthesis were then tested, which were: single material, where both the inside and the outside layer had the mechanical property of an enamel such that the produced prosthesis corresponded to a traditional crown prosthesis having homogenous mechanical properties close to that of the enamel; and graded material, were the inside layer material was defined as the dentin and the outside layer was defined as the enamel to create a two-level graded structure.

Figure 6:
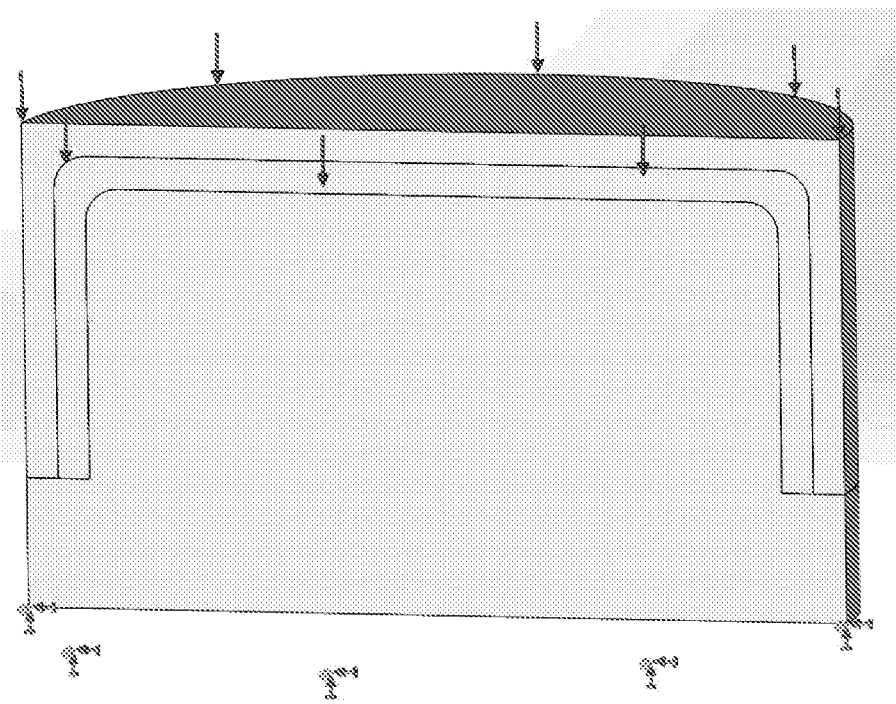
FIG. 6 is a schematic diagram showing a pressure and elastic deformation simulation performed on a dental crown prosthesis model in accordance with the presently-disclosed methods.

After establishing the parameters for the prostheses, to perform the initial evaluation, the structure was then fixed on the bottom of a back support, and 0.69 MPa (100 psi) of simulated pressure was applied onto the top surface of the outer layer. The inter-layer bonding of the crown model as well as the bonding between the inside layer and the back support were both defined as "bonded," indicating no relative motion and penetration. The schematics of the simulation scenario is shown in FIG. 6, but did not include plastic deformation and failure, and only showed the elastic deformation effects.

Figure 7:
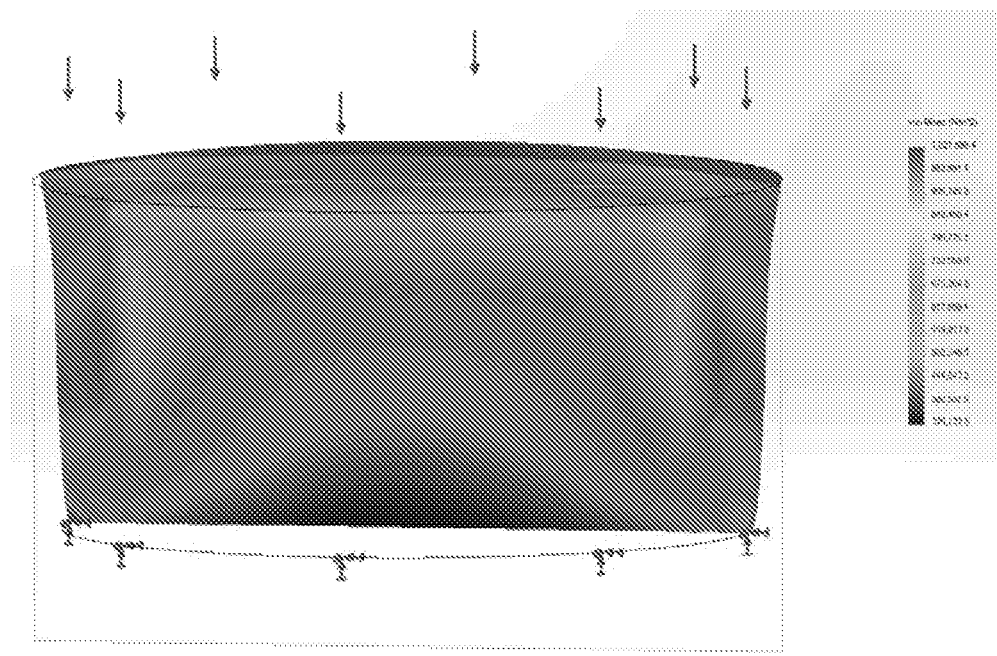
FIG. 7 is a schematic diagram showing the results of a pressure and elastic deformation simulation performed on a dental crown prosthesis model comprised of a single material.
Figure 8:
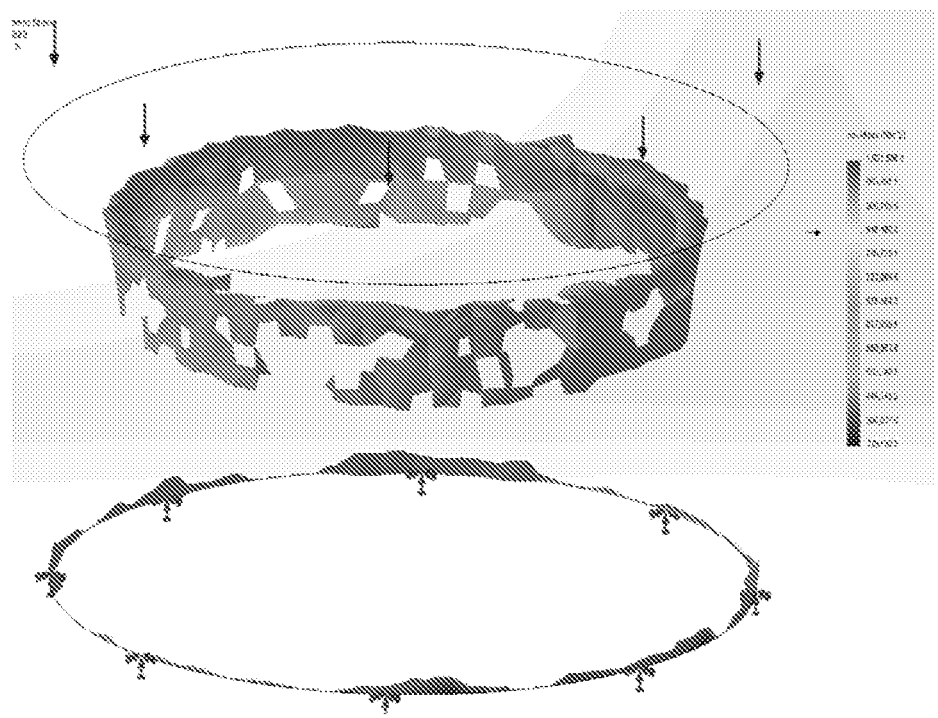
FIG. 8 is another schematic diagram showing the results of a pressure and elastic deformation simulation performed on a dental crown prosthesis model comprised of a single material.

The above-described simulation methods were also used to evaluate a dental crown comprised of a single material. The results are shown in FIG. 7 and FIG. 8. The maximum stress level on the structure was around 1.02 MPa, and the stress level at the interface between the crown and the back support was found to be around 0.85-0.95 MPa, as shown in FIG. 7. The region with a stress level above 0.85 MPa is shown in FIG. 8 with iso-clipping functions in SolidWorks. From the single material simulations, it was apparent that the crown-support interface as well as the root of the support was subject to the most critical stress.

Figure 9:
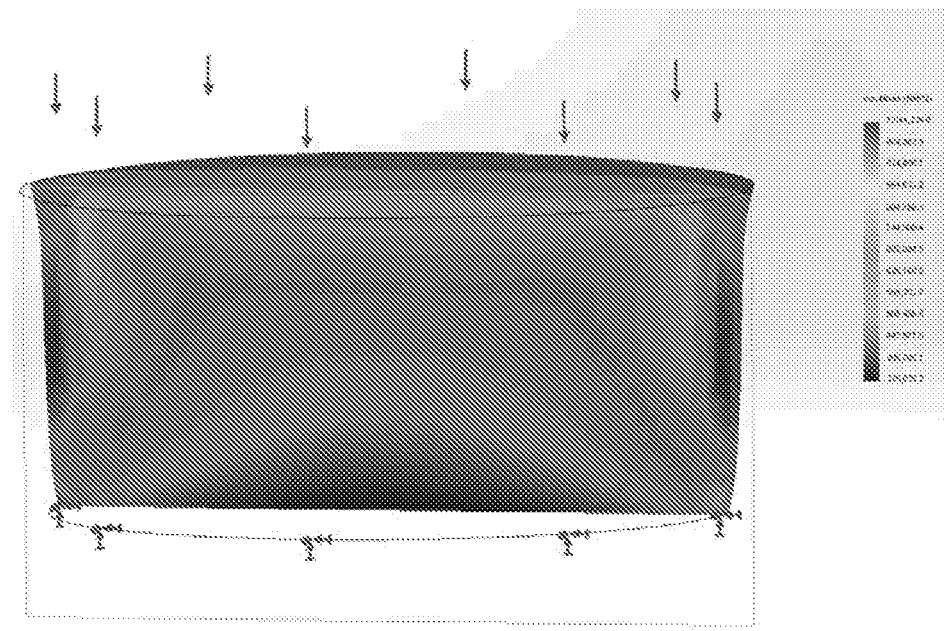
FIG. 9 is a schematic diagram showing the results of a pressure and elastic deformation simulation performed on a graded dental crown prosthesis model.
Figure 10:
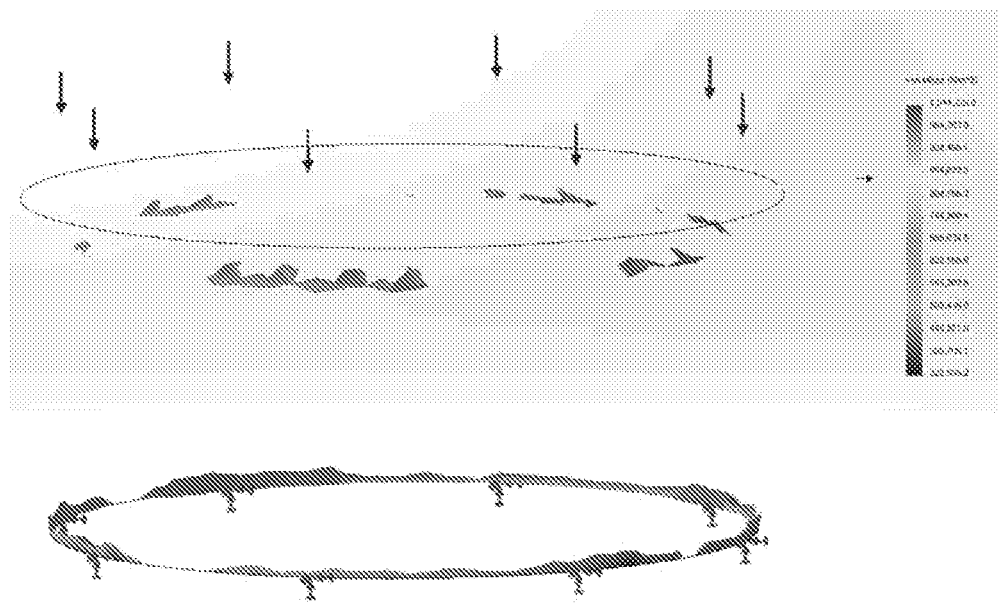
FIG. 10 is another schematic diagram showing the results of a pressure and elastic deformation simulation performed on a graded dental crown prosthesis model.

The above-described simulation methods were then subsequently used to evaluate a dental crown comprised of a graded material. The results are shown in FIG. 9 and FIG. 10. The maximum stress level on the simulated structure was 1.04 MPa, which was slightly higher than the single-material case. In addition, for both cases, the maximum stress level occurred around the edge of the root of the support, and therefore it was not directly located on the crown prosthesis itself. There also existed a stress concentration between the enamel and the dentin layers similar to what was shown in FIG. 8. However, a significantly smaller region with stress levels of 0.85 MPa and above were present in this case, as shown in FIG. 10. This clearly indicated that when a graded material was applied to the dental crown, the stress concentration effect was significantly less spread over the structure, therefore contributing to the potential increase of service life.

Figure 11:
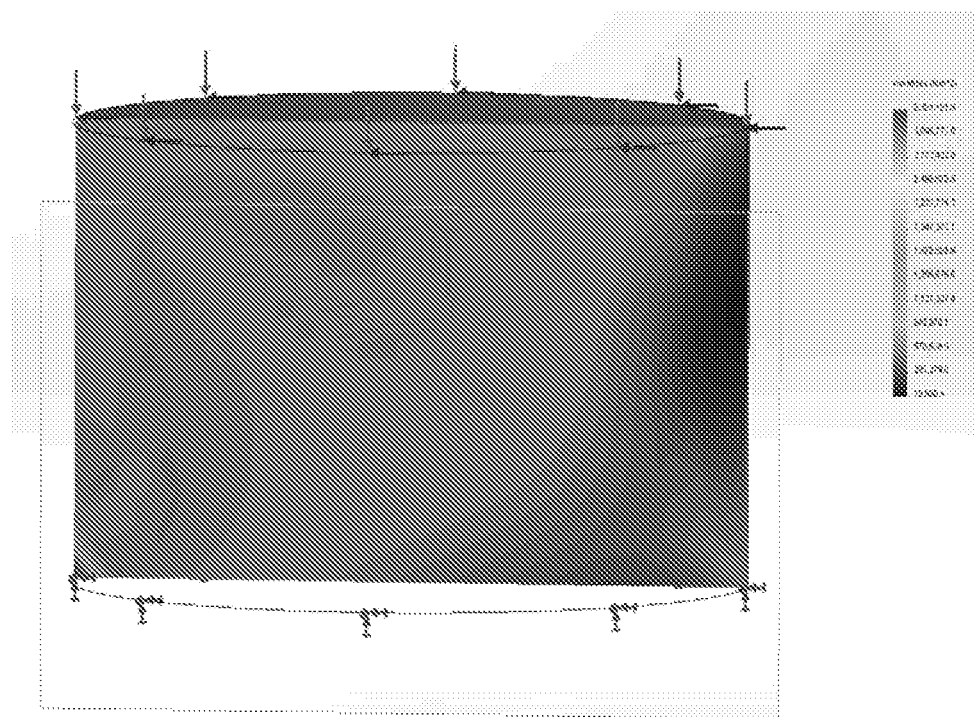
FIG. 11 is a schematic diagram showing the results of a compressive and shear pressure simulation performed on a dental crown prosthesis model comprised of a single material.
Figure 12:
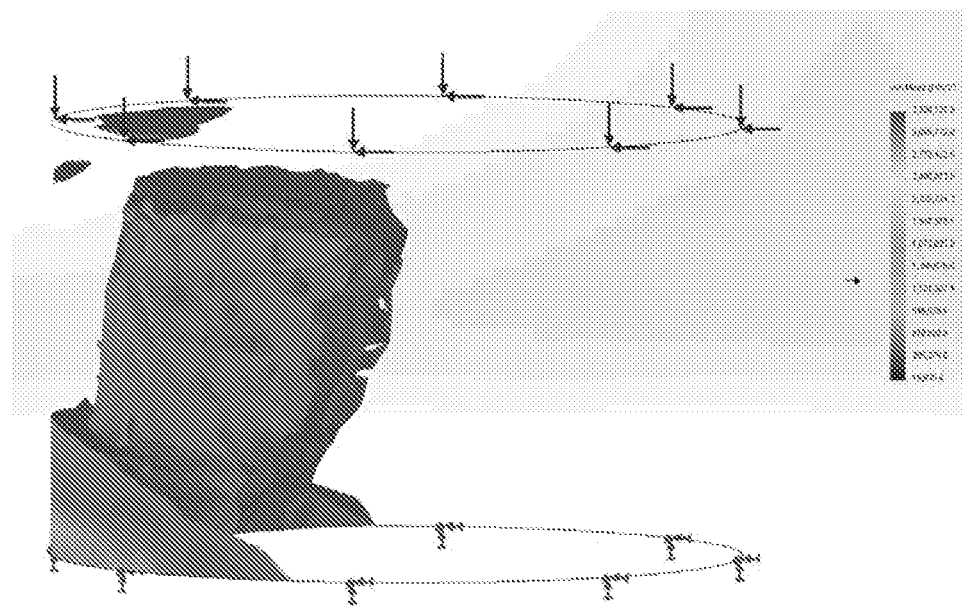
FIG. 12 is another schematic diagram showing the results of a compressive and shear pressure simulation performed on a dental crown prosthesis model comprised of a single material.
Figure 13:
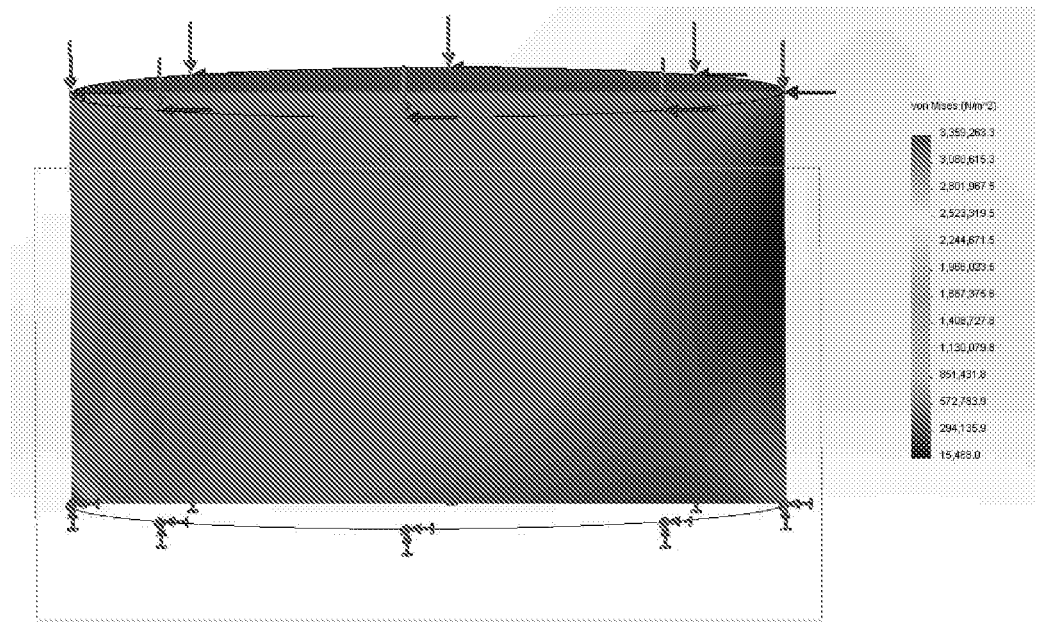
FIG. 13 is a schematic diagram showing the results of a compressive and shear pressure simulation performed on a graded dental crown prosthesis model.
Figure 14:
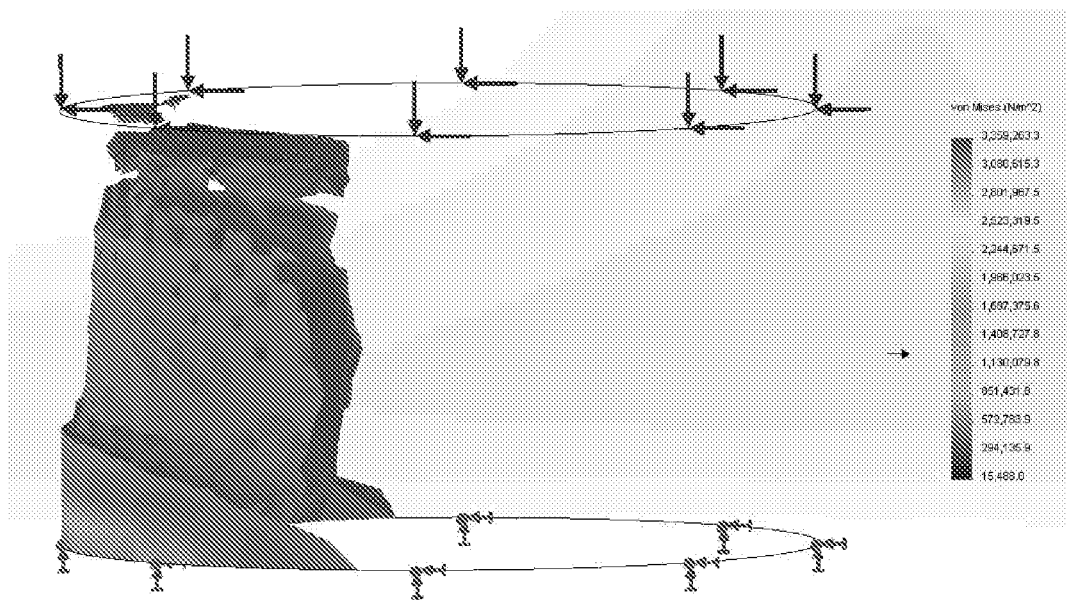
FIG. 14 is another schematic diagram showing the results of a compressive and shear pressure simulation performed on a graded dental crown prosthesis model.

Under normal circumstances, a posterior crown is subject to both normal compressive and shear pressures. As such, an additional set of simulations was performed to assess the compressive and shear pressure that would be experienced. In addition to the compressive stress, shear stress of 345000 Pa (50 psi) was applied on the top surface of the outside layer. The results of the simulation are shown in FIGS. 11-14. FIG. 11 and FIG. 12 show the results for a single material case, and FIG. 13 and FIG. 14 show the results for a graded material case. In both cases the critical stress regions were located at the root of the support. However, the same trend on stress concentration was observed. Comparing FIG. 12 and FIG. 14, the region of stress level higher than 1.25 MPa for graded material crown was smaller than that of the single material crown, which further supported the conclusion that the fabrication and use of a graded structure could improve the mechanical performance of the restoration.

Example 2—Analysis of Graded Dental Porcelain Ceramic Structures

Dental ceramic has been used for denture teeth since 1790 and currently is widely used in dentistry to produce natural-looking tooth restorations due to the numerous advantages of ceramics, such as color, strength, aesthetic, translucency, durability, etc. The major applications of dental porcelain include the fabrication of single unit full coverage ceramic crowns, ceramic crowns and bridgework, inlays, onlays, labial facing veneers, supporting bars, and denture teeth. There exist two basic types of ceramic restorations—all-ceramic and metal-ceramic. The all-ceramic systems generally comprise a body made from ceramics instead of the traditionally used metals, and sometimes at least one additional porcelain layer. All-ceramic systems are made from a ceramic with substantial crystal content from which their higher strength and toughness are obtained. These material systems can provide more natural translucency with no loss of mechanical strength, therefore have drawn increasing interest in the past two decades. Currently the all-ceramic restorations are fabricated by either a press technique (lost wax technique), slip casting, or more accurate CAD-CAM method. In the CAD-CAM method, the ceramic feedstock are pre-sintered and then milled with a CNC milling machine using special diamond tool. Then, in some cases, the machined parts are further sintered to acquire the final density and appearance. On the other hand, metal-ceramic systems are still commonly used. In these material systems, several layers of porcelain powder in aqueous slurry are sequentially fused to a metal framework to simulate natural teeth. These layers have three different levels of translucency. The first and opaque layer is used to mask the dark metal substrate. The intermediate layer, the so-called dentine, is the principal bulk construction of the artificial tooth structure and is also used to provide translucency of the porcelain. The upper and most translucent layer is called the enamel or incisal porcelain. Each layer must subsequently be fused in an electric or vacuum furnace at about 900° C. in most cases to obtain the optimal properties.

Currently one of the biggest disadvantages of ceramic materials including dental ceramic and porcelains is its low toughness. This drawback causes most of the failures in both types of aforementioned ceramic restorations. In general, failures in ceramic restorations could be categorized into three groups, chipping, bulk fracture, and interface delamination. Chipping failure could occur in both types of restorations, and bulk fracture mainly occurs in the all ceramic restorations, both due to the brittleness of dental ceramics. Interface delamination occurs in the interface of metal-porcelain restorations because of weak bonding between metal and porcelain. FIG. 15 and FIG. 16 show the chipping and bulk fracture in porcelain restorations created under biting forces.

It is appreciated that natural teeth have graded structures, meaning that their properties are not the same in different regions. Indeed, natural teeth have a relatively soft core and a harder surface (graded structure), which is speculated to be one of the main reasons for good fracture resistance properties exhibited by natural teeth. In this regard, and as outlined above, with the capability of producing graded structures directly from a CAD model with adequate accuracy and minimal waste, additive manufacturing (AM) was believed to be able to allow for the fabrication of dental restorations with both colors and properties that mimicked natural teeth. As such, with binder jetting 3D printing (3DP) process being relatively less commonly used for direct manufacturing of functional parts, the process was believed to offer some potential advantages in ceramic printing, such as flexibility with different ceramic materials, high feature resolution, and process control, and thus, binder jetting was adopted to fabricate and analyze graded dental porcelain ceramic structure. In particular, the ExOne M-Lab was utilized in an attempt to fabricate graded structure samples from off-the-shelf commercial porcelain and alumina powders used commonly for dental applications, with the microstructure of the produced samples and the integrity of bonding created between different compositions then characterized in detail.

Briefly, in the studies, off-the-shell dental porcelain was used as the base material, and alumina powder was used as the additive to the base material for graded composition control. Alumina was selected as the additive since it is one of the main ingredients of the current dental porcelain materials, and therefore does not pose additional material compatibility issues. Table 2 shows the compositions of the pure porcelain used in this research. In order to evaluate microstructural and mechanical properties, laminate structures with dimensions of 25×2×1.5 mm were designed according to ASTM C1161-13. Due to the limitation of the powder bed based AM systems with multi-material printing, two different procedures were taken for the fabrication of these samples in graded compositions, namely lamination stacking and continuous fabrication. For the lamination stacking method, samples with two different compositions were printed separately and stacked together in a way that their total thickness was 1.5 mm. A thin layer of the binder was applied manually between two compositions in the attempt to help form a good bonding between layers in the sintering stage. On the other hand, for the continuous fabrication method, the first laminate was printed out with powders with the first composition, then the process was paused to change the powder supply into the powders with the second composition. After the powder change, the process was resumed, and therefore, the graded structure was directly formed by the printing process. In the study, the two compositions used were pure porcelain and porcelain containing 10% wt. alumina (10% alumina porcelain). As such, for the continuous fabrication, the feed chamber of the machine was filled with pure porcelain first, and a sample with thickness of 0.75 mm was printed in the build chamber. After the first part of the sample was printed, the feed chamber was completely cleaned and refilled with the 10% alumina porcelain. Thereafter, 10% alumina porcelain was printed over the pure porcelain in the build chamber with the thickness of 0.75 mm.

10% vt. flow agent was also added to the pure porcelain for improving the overall powder flowability by serving as a lubrication interface. Surface-modified R972 $SiO_2$ powder (COSMOS Plastic & Chemicals, Mumbai, India) was used as the flow agent. The powder was composed of greater than 99.8% fumed silica treated with dimethyldichlorosilane (DDS), with an average particle size of 16 nm. Due to the small particle size and low packing density of this flow agent, it was expected that the addition of the flow agent would not have a significant effect on the microstructure and mechanical performance of the dental porcelain. The system used for the fabrication was the ExOne M-Lab, and the binder used for the process was the ExOne PM-B-SR1-04, an ether solvent based binder, which was originally developed for stainless steel, but was found to be suitable for the dental porcelain.

TABLE 2

Chemical composition of used dental porcelain

| $SiO_2$ % | $Al_2O_3$ % | $K_2O$ % | $Na_2O$ % |
|---|---|---|---|
| 55-61 | 13-16 | 11-15 | 4-6 |

After printing, the specimens were subsequently dried in an oven at 150° C. for 1 hour. Dried samples were then sintered in the furnace. For this purpose, samples were held at 500° C. for 30 minutes to burn out the binders and then at 850° C. for another 30 minutes for sintering. The sintering route selected for this study was based on the results from the preliminary process development of the same material. The sintered samples were then used for microstructural characterizations. In order to analyze the microstructure of each compositions as well as bonding integrity between two compositions, the specimens were polished, etched with 5% hydrofluoric acid (HF) for 30 s, and finally sputter-coated with palladium. SEM and EDAX systems were then utilized to take microstructure images and to determine the compositions of the specified areas, respectively.

Dental porcelains are normally composed of silica, glass modifiers, feldspar, and coloring agents, with silica being contained in dental porcelain in two different forms. The first type is in the form of amorphous feldspathic glass that consists of silica, alumina and a flux. In this type of porcelain silica is the major glass former in the porcelain. The second type of silica is in the form of refractory crystalline quartz particles which are dispersed through the glassy phase to act as pinning points for crack propagations. One example of the second type is the Feldspar, which is a naturally occurring glass that contains silica, fluxes and alumina, all bound together. The phase diagram of a typical dental porcelain is shown in FIG. 17. As can be observed, depending on the sintering temperature and the composition, porcelain may have different phases. Since the samples were sintered at 850° C., according to the diagram it is expected to have Potash Feldspar and Tridymite (Silica crystals) in the microstructure.

Figures 18A, 18B:
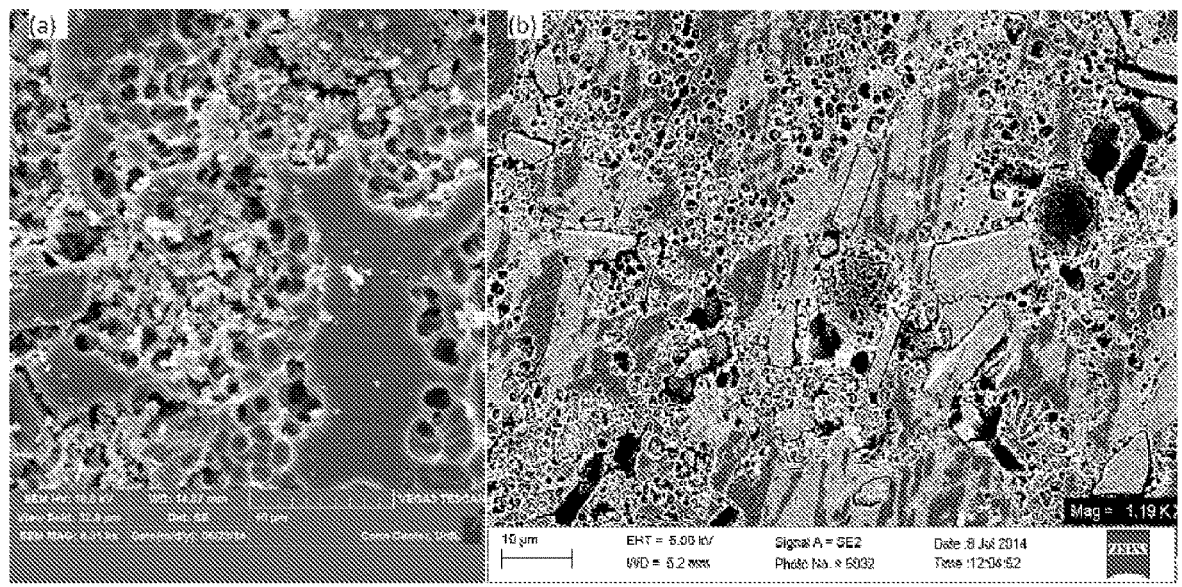
FIGS. 18A-18B include images showing the microstructure of pure porcelain (FIG. 18A) and 10% alumina porcelain (FIG. 18B) after sintering at 850° C. for 30 minutes.
Figure 19:
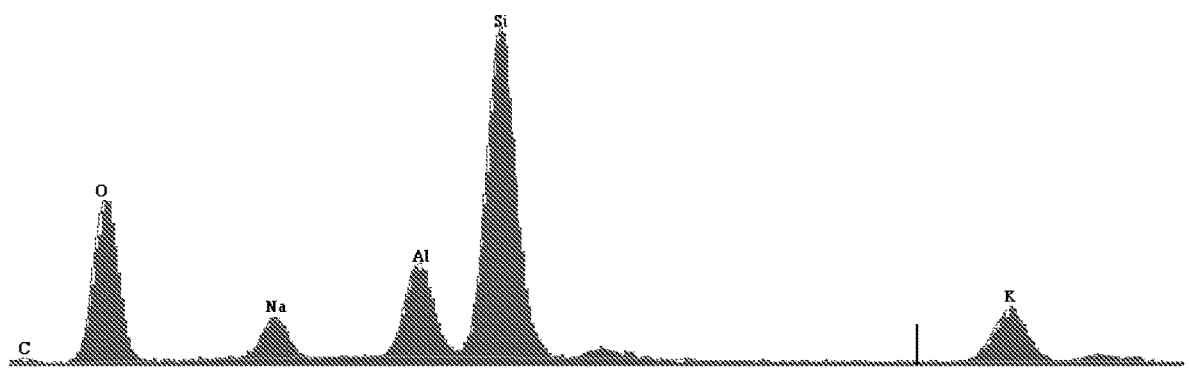
FIG. 19 is a schematic diagram showing an energy-dispersive X-ray spectroscopy (EDAX) analysis of a pure porcelain microstructure.

FIGS. 18A-18B shows the SEM microscopy of the pure porcelain and 10% alumina porcelain samples. From FIG. 18A, the tiny alumina and silica crystals were completely surrounded by glassy matrix in pure porcelain microstructure. Silica crystals can barely be observed in the glassy matrix due to its similar refractive indexes compared to the glassy matrix. EDAX analysis of the pure porcelain matrix is presented in FIG. 19. In addition to Si and Al which are dominant elements as explained, K and Na elements can be observed in the microstructure. These elements are represented as Potassium oxide ($K_2O$), Sodium oxide ($Na_2O$) in the microstructure and act as a modifier or flux, which is commonly regarded as a mineral that melts at a low temperature and functions to lower the function temperature of dental porcelain by interrupting the integrity of the silica network. In this regard, and without wishing to be bound by any particular theory, with the addition of $K_2O$ and $Na_2O$, it was believed that some of the silica tetrahedral covalent bonds will be broken to allow the atoms to move more easily at lower temperatures, and, as a consequence, the improved mobility was then believed to be responsible for the decreased viscosity and lower softening temperature.

FIG. 18B shows the microstructure of 10% alumina porcelain via a micrograph taken by back-scatter detector. The difference between the microstructures of pure porcelain and the 10% alumina porcelain was a result of alumina crystal formation. The addition of alumina crystals to the feldspathic glass matrix would result in an increase in the flexural strength of the material, since crack propagation through the alumina particles requires higher stress-levels. Depending on the strength of the bond between the reinforcing particles and the glassy matrix, cracks can be diverted around the alumina crystals rather instead of propagating along the original directions. As a result, more tortuous crack paths are produced, which enhances the strength of the porcelain. Moreover, the alumina crystals also imparted rigidity to the structure at elevated temperatures, reducing the chances of distortion and shrinkage when the lower softening point materials were added. The reduced shrinkage can have several beneficial effects. With less shrinkage, the stresses generated in the porcelain during firing could be reduced and, consequently, the likelihood of microcrack formation would be less, and the resulting restorations would be stronger and tougher.

Figure 20:
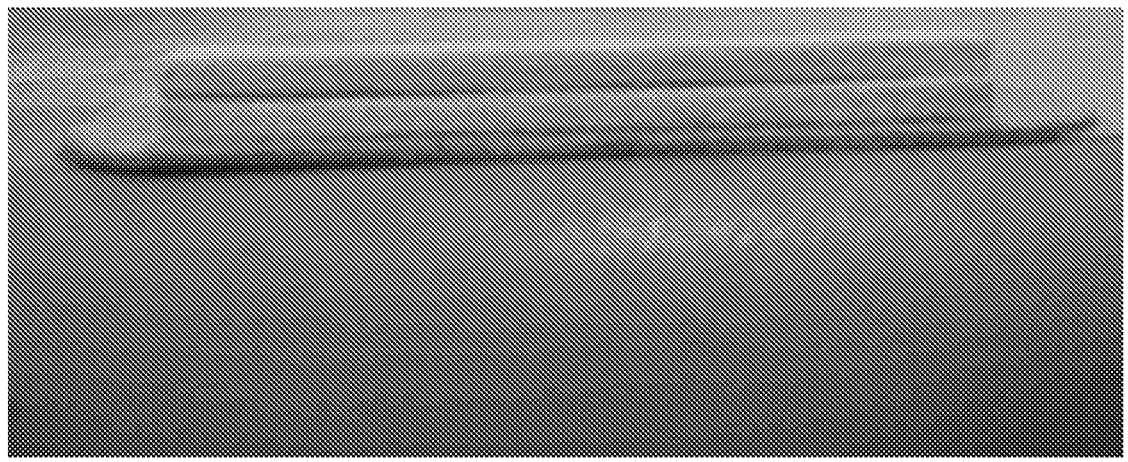
FIG. 20 is an image showing a graded structure sample produced by a lamination stacking method according to the presently-disclosed subject matter before undergoing sintering.

FIG. 20 shows a sample before sintering produced by the lamination stacking method. As can be observed, a weak bonding was created between two compositions, and delamination was obvious despite the manual application of binder between the two laminates before the sintering. It was believed that the lack of initial bonding which would be formed during the printing and in-process drying, as well as the differences between thermal expansions and tendency of ceramics to slump during sintering, are two likely causes for the delamination.

Figure 21:
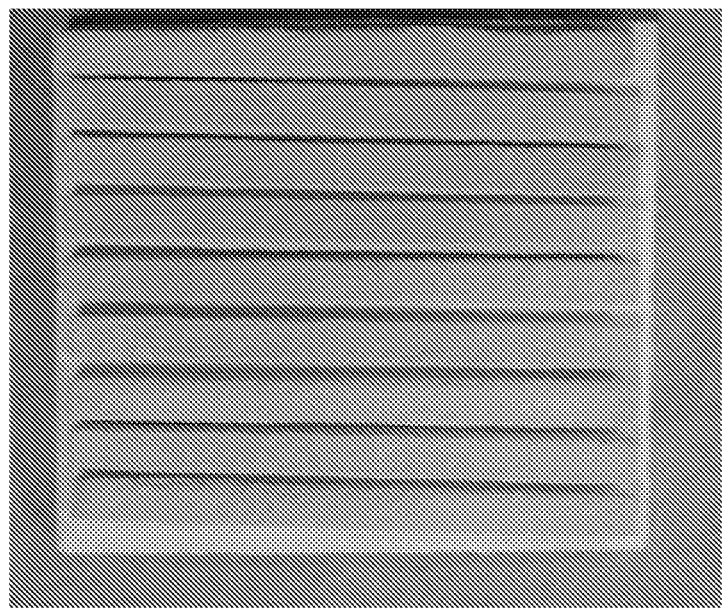
FIG. 21 is an image showing a graded structure sample produced by a continuous method according to the presently-disclosed subject matter before undergoing sintering.

The samples produced by the continuous method described above are shown in FIG. 21. With this method, good bonding could be visually observed between two laminations after the sintering. FIG. 22A shows the microstructure of the specimens with pure porcelain and 10% alumina porcelain fabricated by continuous fabrication method. In addition, the microstructure of 10% alumina porcelain at higher magnification is shown in FIG. 22B. As can be observed, feldspar glass is dominant in the microstructure. Also, only one side of the sample appeared to contain alumina crystals dispersed uniformly in a glassy matrix. These crystals ranged in size from approximately 2 to 20 μm. From FIGS. 22A-22B, it was also clear that there was no distinguishable interface between these two compositions, which indicated that good bonding had been created between pure porcelain and the 10% alumina porcelain composition. The only distinct difference between two microstructures was the amount of the alumina crystals which was higher in one side than other.

Figure 24:
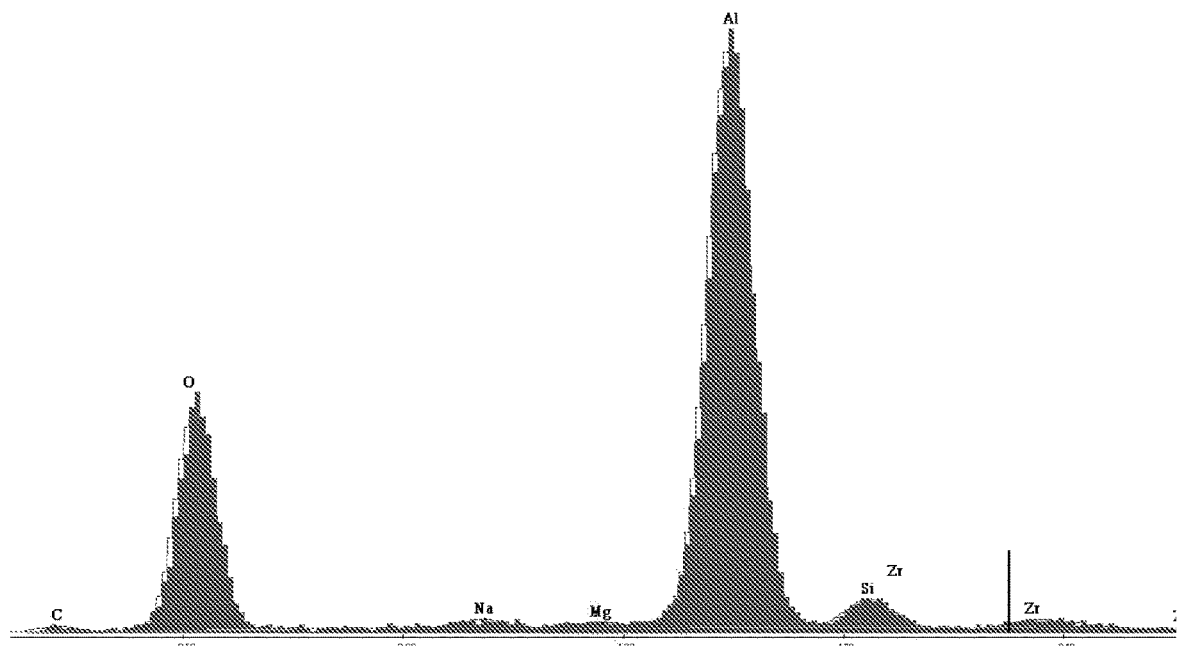
FIG. 24 is a schematic diagram showing EDAX results of crystals observed in the microstructure of a porcelain structure produced in accordance with the presently-disclosed subject matter.

The presence of alumina crystals in one side of the sample was confirmed by two methods, morphology and EDAX. FIG. 23 shows the SEM microscopy of the alumina powder. As it can be observed, the dispersed crystalline phase in the microstructure of porcelain (FIG. 22B) has the same morphology and size range as the crystals in FIG. 23. EDAX results also clearly suggested that the crystals observed in the microstructure are alumina particles, as is shown in FIG. 24. Therefore, it was concluded that the graded structures were successfully fabricated by the 3DP process and retained after the sintering.

It was further believed that since the crystalline alumina concentration in one side was greater than that of the other side, for complete sintering a lower viscosity glass would be necessary to avoid residual porosity. In fact, some porosity was evident in both sides from FIGS. 22A-22B. The pure porcelain side contained less pores, which appeared as black areas on the back-scattered electron micrographs. Porosity in the side with 10% alumina addition was largely associated with the un-melted alumina crystals during the sintering.

In summary, in the foregoing study, the binder jetting 3DP process was adopted to produce porcelain parts with graded structure. For that purpose, the ExOne M-Lab machine was utilized to print out the samples. A process route that enables direct fabrication of graded dental ceramic structures was demonstrated. Microstructural tests were conducted to evaluate the integrity of bonding between layers of two different compositions of the fabricated graded structures. Presence of alumina crystals in only one side of the microstructure was confirmed by EDAX analysis and SEM microscopy. In addition, it was found that good bonding was created between the two compositions using the 3DP process, which further supported the use of the process for the direct fabrication of high quality graded ceramic structures.

Example 3—Analysis of Ceramic Dental Porcelain Materials Using a Three-Dimensional Print (3DP) Process Additional experiments were undertaken to further explore the feasibility of using a 3DP process for high accuracy manufacturing of dental ceramic porcelain structures. In particular, the additional experiments were undertaken to evaluate the processing and post-processing parameters for high accuracy part fabrication with dental porcelain materials. In this regard, the relationships between linear shrinkage, porosity and microstructure of the printed dental porcelain structure and various process parameters were investigated through experiments in order to find the proper parameter sets and understand the influence of each parameter on part quality.

For powder preparation, the material used was IPS InLine Dentin powder (Manufacturer: Ivoclar Vivadent Corporate, Principality of Liechtenstein), which was a commercial product for artificial dental restorations such as crowns, veneers and onlays. The chemical composition and relative basic properties of IPS InLine Dentin powder provided by the manufacturer is shown in Table 3 below.

TABLE 3

| Technical data of dentin powder. | |
|---|---|
| Standard composition (in wt %) | $SiO_2$: 59.5-65.5, $Al_2O_3$: 13.0-18.0, $K_2O$: 10.0-14.0. $Na_2O$: 4.0-8.0, Other oxides: 0.0-4.0, Pigments 0.0-2.0 |
| Flexural Strength | 80 ± 20 MPa |
| Chemical solubility | <100 μg/cm$^2$ |
| Glass transition temperature | 585 ± 10° C. |
| Coefficient of thermal expansion (25-500° C.) | 2 firings: 12.60 ± 0.5 $10^{-6}$ $K^{-1}$ 4 firings: 13.20 ± 0.5 $10^{-6}$ $K^{-1}$ |

Figure 25:
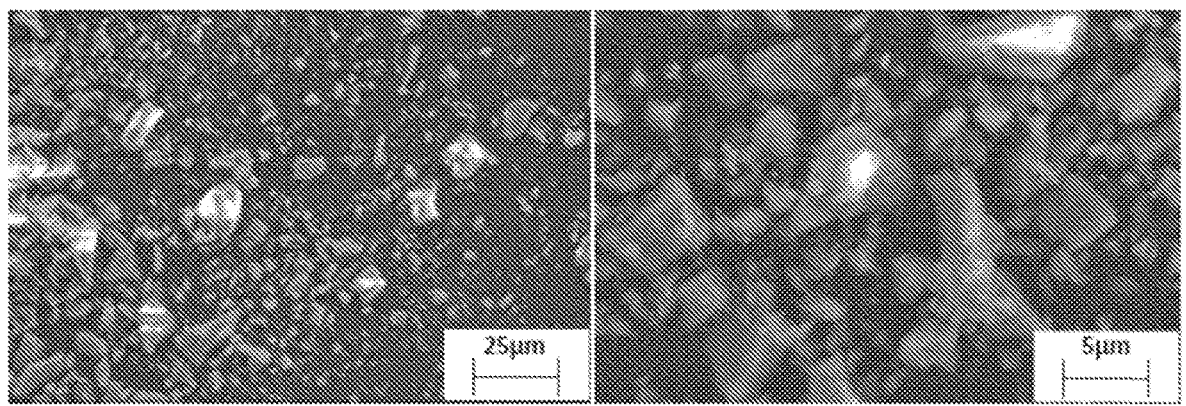
FIG. 25 includes images showing the morphology of dentin powder as analyzed by SEM.

The original powder exhibited significant aggregation, which made it unable to be spread uniformly in the printing process. From the SEM microscopy, the IPS InLine Dentin particles had irregular shape and different sizes ranging from 0.3-10 μm, as shown in FIG. 25. Laser-based particle size analysis (PSA, Microtrac S3000) showed that the characteristic size of the aggregation was approximately 36 μm, shown in FIGS. 26A-26B. It was found previously that the irregular morphology and large particle size range significantly reduced its flowability. In order to improve the flowability of the powder, a flow agent was added. The function of the flow agent was analogous to the addition of sand between two surfaces, and served as low friction contact media and therefore reduced the resistance of relative motions between the powder particles. The chemical composition of the flow agent was largely irrelevant to its primary functionality, and therefore a flow agent with a composition similar to the original powder was selected.

The flow agent chosen was Aerosil R 972 Hydrophobic fumed silica powder (COSMOS Plastic & Chemicals), with an average particle size of 16 nm. This powder was composed of 99.8% fumed silica after treated with dimethyldichlorosilane (DDS) based on a hydrophilic fumed silica with a specific surface area of 130 m$^2$/g (Aerosil R 972 MSDS).

Up to 10% volume percentage flow agent was measured and added to the original IPS InLine Dentin powder, and the container with the mixture was shaken by hand until well-proportioned mixed powder was visually discernible. The flowability was evaluated using both angle of repose and particle size analyzer for the original powder and treated powder with flow agent additive.

Figure 26A:
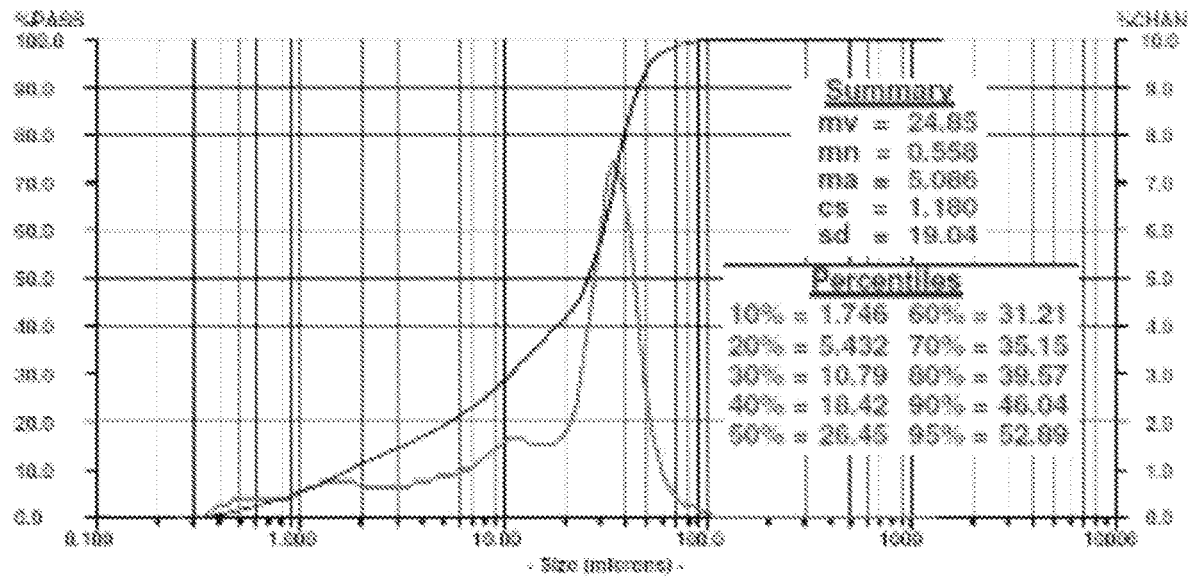
FIGS. 26A-26B includes graphs showing particle size analysis results of dentin powder before (FIG. 26A) and after (FIG. 26B) the addition of a flow agent to the powder.
Figure 26B:
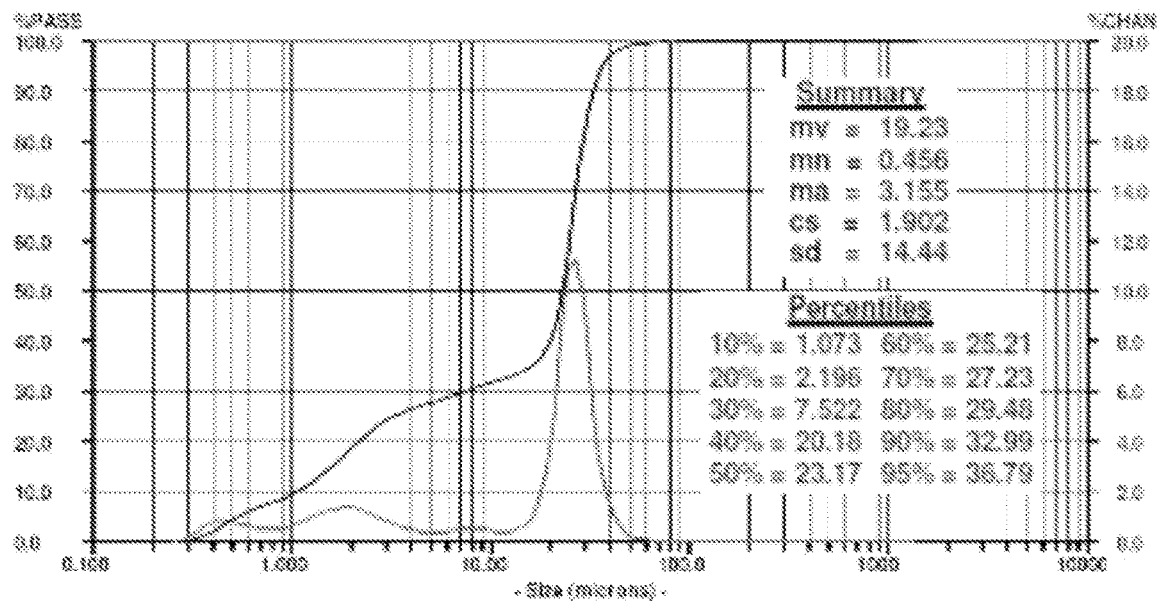

From the results of particle size analysis, flow agent had a significant effect on aggregation. In FIG. 26A, it can be seen that the mean particle size of the original powder was about 25 μm, and the 95 percentile particle size was 52.89 μm. After adding flow agent, the average particle size reduced to about 19 μm as shown in FIG. 26B, and the 95 percentile particle size also decreased to 36.79 μm.

Figure 27:
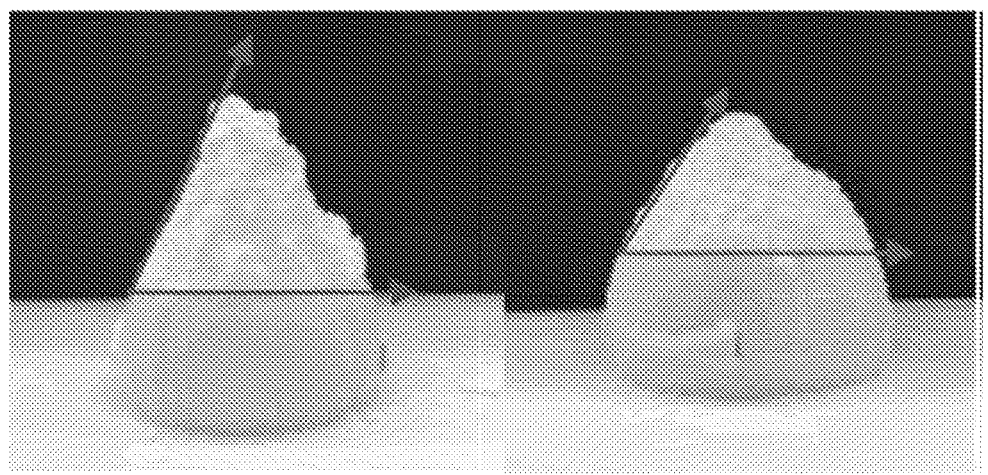
FIG. 27 is an image showing the angles of repose in original dentin powder (left image) and in dentin powder after the addition of a flow agent.

The angle of repose test also showed significant improvement of flowability with the prepared powder. The comparison of angles of repose of the original powder and the one with flow agent additive is shown in FIG. 27, and the measurement results are listed in Table 4 below. The addition of 10% by volume flow agent significantly reduced the aggregation and flowability issue of the original powder. This was further verified with a preliminary trial, and was consequently used as the standard powder preparation method for the remainder of the study.

TABLE 4

Angles of repose of powder.

| Powder type | Angle of repose (degree) |
| --- | --- |
| Original | 67 |
| 10% (vt.) addition of flow agent | 58 |

Figure 28:
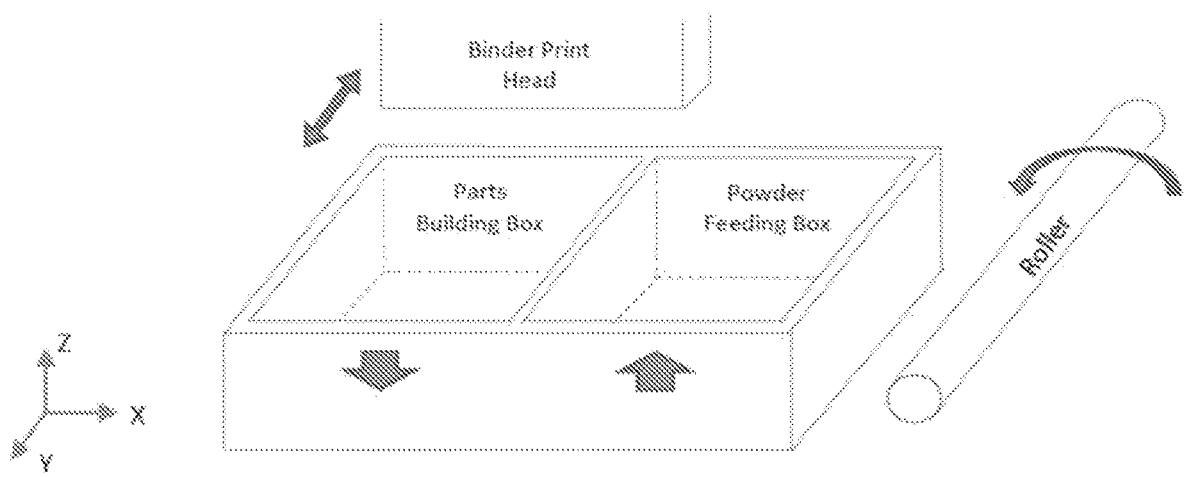
FIG. 28 is a schematic diagram showing a 3D printing process for an ExOne M-lab system used in accordance with the presently-disclosed subject matter.

The ExOne M-Lab system was used for this study, which is a powder bed based binder jetting 3DP process. During the process, binder liquid infiltrates into the powder bed and bonds the powder particles to create the geometries. After the printing operation of each layer, the powder bed is heated by an infrared heater for a set amount of time in order to partially cure the binder and to gain necessary strength. For each new layer, the powder was fed from the powder feeding box via a roller. The procedures were repeated until the parts were completed. The schematic of the ExOne 3DP process is shown in FIG. 28.

The M-Lab system used two parameters for the control of binder amount and drying level, which were the power level and the saturation level. The default setting for those two parameters were 60% power level and 70% saturation, which was developed for stainless steel powder. In order to identify suitable parameters for the dental porcelain powder, additional experiments were performed. Two sets of cubic specimens with a size of 10×10×10 mm were designed and fabricated under different power levels and saturation levels. The fabricated green parts were put into a drying oven and baked at 200° C. for 2 hours to fully cure the binder.

Figure 29:
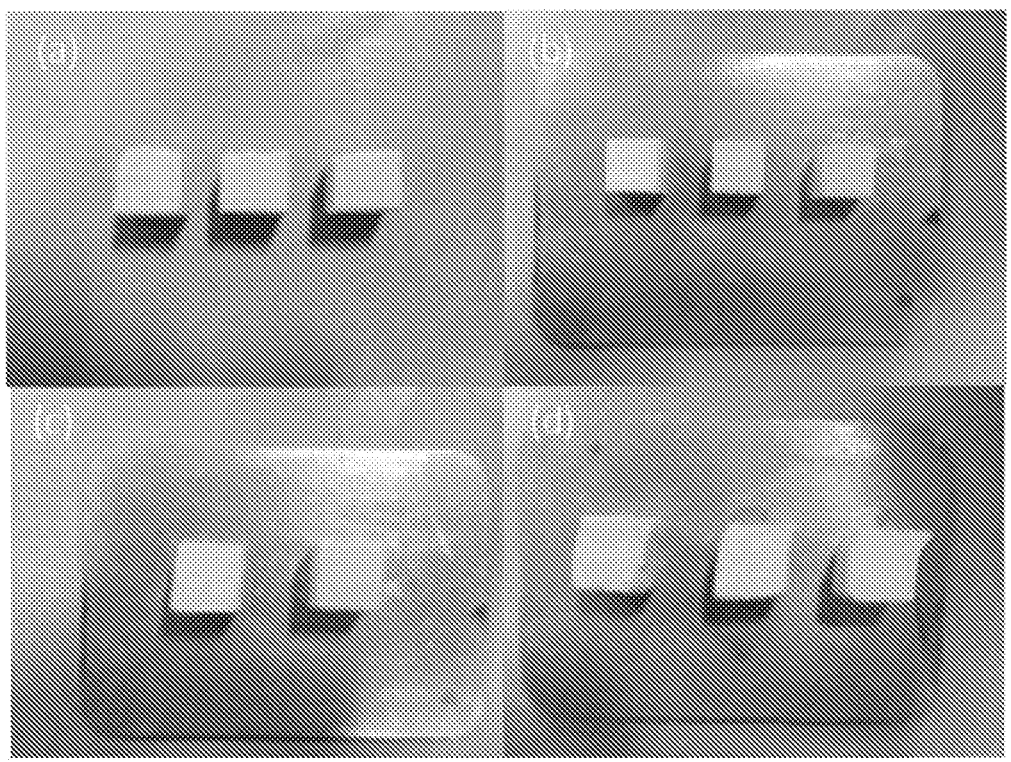
FIG. 29 includes images showing porcelain structures printed using binder saturation levels of 45% (panel (a)), 50% (panel (b)), 60% (panel (c)), and 70% (panel (d)).
Figure 30:
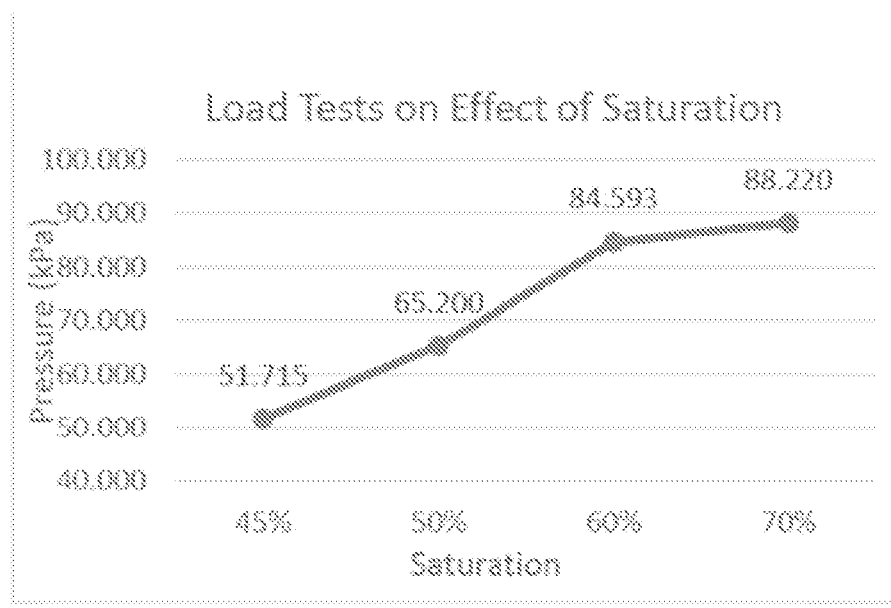
FIG. 30 is a graph showing the maximum compressive load of fabricated porcelain structures under different saturation levels.

The first set of experiments evaluated the effect of saturation level on the print quality of the porcelain powder. The binder saturation levels were set at 45%, 50%, 60% and 70%, respectively, with the power level fixed at 60%. The printed samples with the various saturation levels are shown in FIG. 29. From these results, it was apparent that the saturation level could significantly affect the geometry of green parts. When the saturation level was set as 70%, the printed parts deformed in the direction of roller spreading. This was likely caused by insufficient drying of binder and the resulting low strength of the printed area, which could be displaced under the frictional force of the roller when a new layer of powder is deployed. As the saturation level reduced, less distortion was observed. On the other hand, when the saturation continued to reduce to 45%, the amount of binder became insufficient, and the strength of green parts was so low that the parts could not be handled without damage. A quick loading test was performed on the green parts to evaluate the maximum compressive force that could be applied to these parts without significant damage. A flat plate was placed on the top of the samples, and weight was gradually added to the plate until the sample crumbled. The results are shown in FIG. 30, and it was apparent that when fully cured, the strength of the green part increases with the increase of binder amount. When the saturation level reduces from 50% to 45%, there was an approximately 25% reduction of green part strength, which supported the experimental observation.

Figure 31:
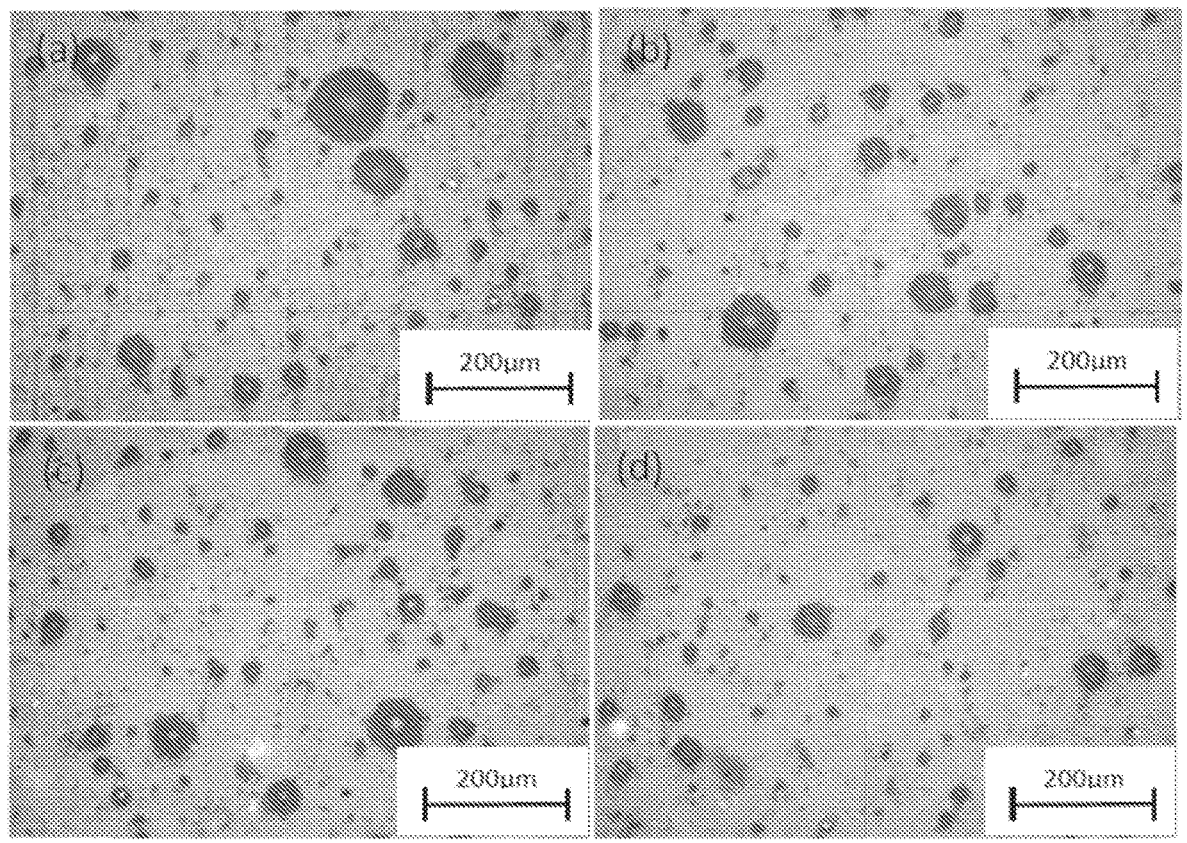
FIG. 31 includes images showing the microstructure of fabricated porcelain structures produced with a heating treatment of 850° C. for 30 min and with binder saturations of 45% (panel (a)), 50% (panel (b)), 60% (panel (c)), and 70% (panel (d)).

In order to analyze the effect of saturation level on the quality of final parts after sintering, the same set of green parts were sintered at 850° C. for 30 minutes. Specimens of each saturation level were sectioned at mid-plane along the vertical direction and polished for optical microscopy (Olympus MX51). Pore distributions were observed under microscopy, as shown in FIG. 31 with 200× magnification. From the microscopy, the size of pores of samples with 45% saturation level ranged from 5-150 μm, while the pores in samples with 70% saturation level were considerably smaller with a maximum size of approximately 45 μm. The maximum pore diameters become smaller as the saturation level increased, but the total porosity did not seem to change significantly. One possible cause of the porosity increase at lower saturation level was the surface void formation during the powder deposition by the roller, which resulted in the lower binding strength. The addition of the flow agent might have also contributed to the porosity, as the flow agent particles might result in lower binder wettability due to the hydrophobic surface. Based on the analysis of porosity in different saturation levels, 50% saturation was chosen for further study since it yielded adequate handling strength and minimized in-process part distortions.

Figure 32:
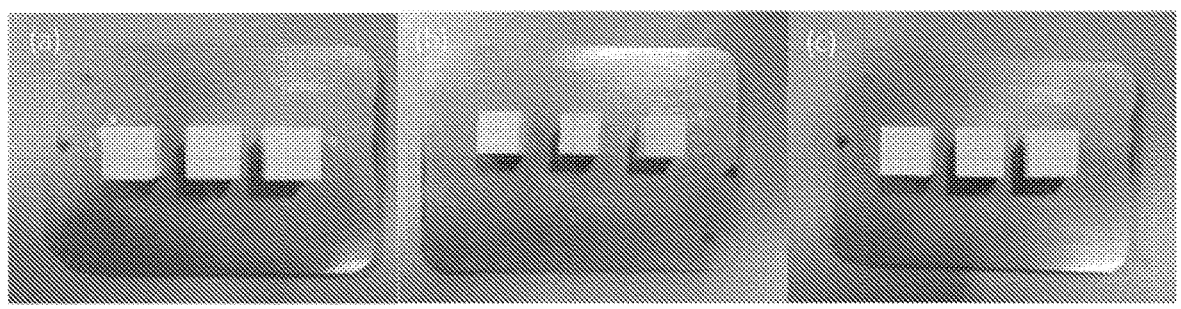
FIG. 32 includes images showing fabricated porcelain structures printed at power levels of 55% (panel (a)), 60% (panel (b)), and 65% (panel (c)).
Figure 33:
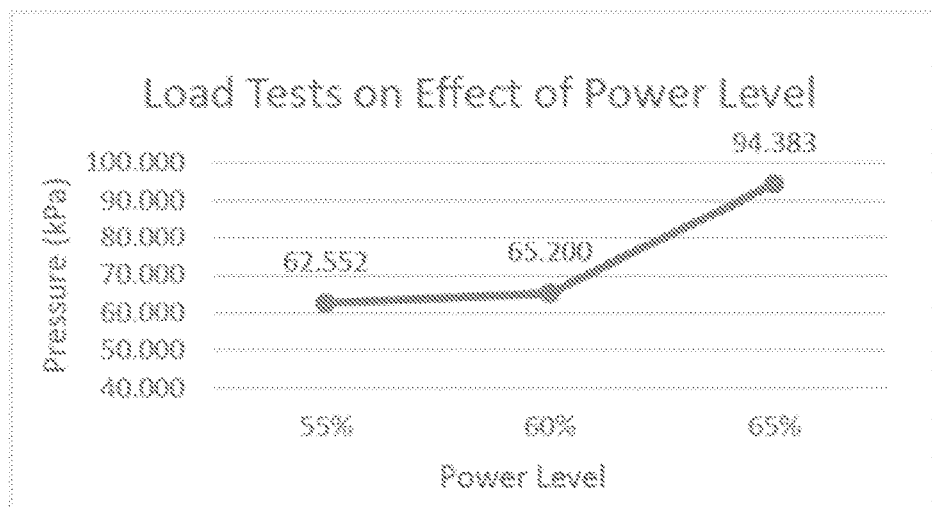
FIG. 33 is a graph showing the effect of power level on the compressive strength of the fabricated porcelain structures.
Figure 34:
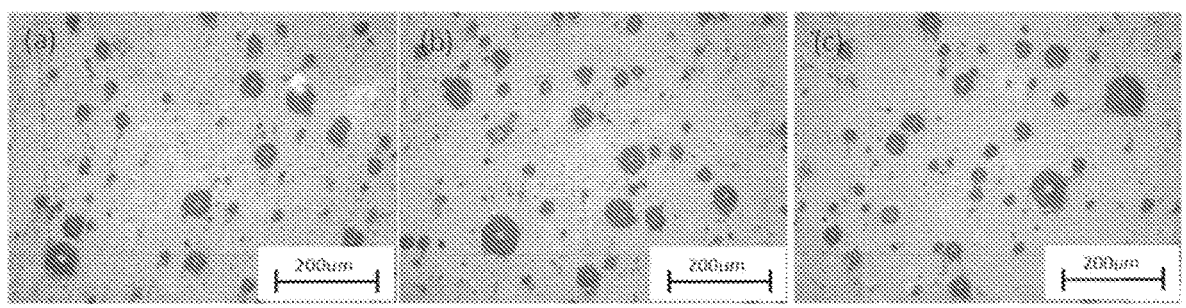
FIG. 34 includes images showing the microstructure of fabricated porcelain structures producing using a heating treatment of 850° C. for 30 min and with power levels of 55% (panel (a)), 60% (panel (b)), and 65% (panel (c)).

Since the powder bed was cured after each layer was printed, it was believed that the power level could potentially have significant influence on the in-process part qualities. Therefore, in the second set of experiments, the power levels were set as 55%, 60%, and 65% while the saturation levels were kept at 50%. The printed samples are shown in FIG. 32. From the measurement results, the power level did not seem to have apparent effects on the geometrical accuracies of the green parts. The same set of samples was also sintered at 850° C. for 30 minutes and prepared in the same way for microscopy. The loading test of the green parts at all three power levels yielded adequate strength as shown in FIG. 33, while higher power levels appeared to be more advantageous. On the other hand, higher power level corresponded to an increase of drying time, which was significant due to the fact that the powder bed was dried at every layer. The microstructure of the samples is shown in FIG. 34, and there was also no significant dependence between the power level and the porosity of the final parts. Without wishing to be bound by an particular theory, it was believed that this might be explained by the relatively low saturation level used for these studies. It could be reasonably assumed that the binder could be adequately cured at the range of power levels experimented with (e.g. 55%-65%), therefore no significant difference could be observed on the green parts. It could also be expected that at higher saturation levels, higher power level might be needed to achieve satisfactory handling strength. Therefore, based on the preliminary experimental results, 60% power level was selected as the standard parameter for further study.

Figure 35:
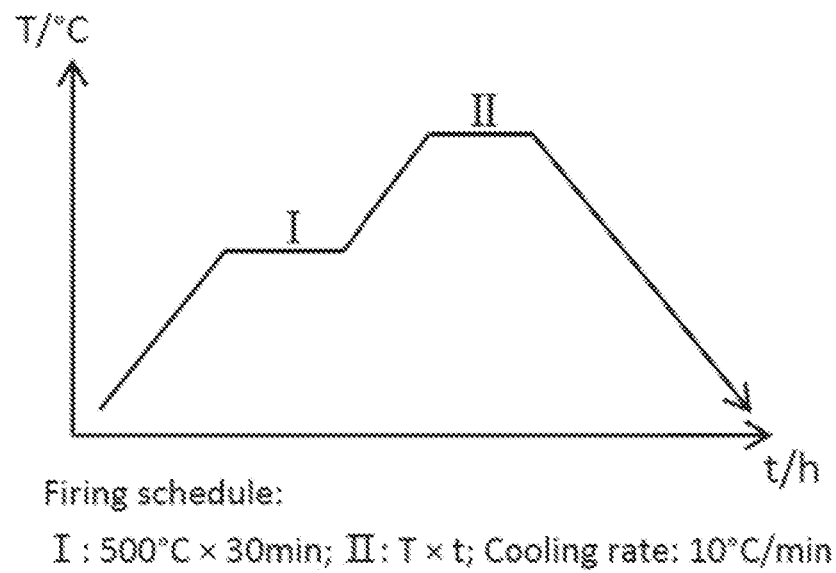
FIG. 35 is a graph showing an exemplary firing (e.g., sintering) schedule used in accordance with the presently-disclosed methods.

After the printed green parts were fully cured in the drying oven at 200° C. for 2 hours, they need to be cleaned and sintered to achieve the desired strength and density. A general firing schedule for dental porcelain ceramic is shown in FIG. 35. The firing process started at room temperature, and heated at a set rate to 500° C. for half an hour (phase I), which aimed for burning out the binder completely. After the burnout step, the part continued to be heated to the target sintering temperature and subsequently held for a set amount of time (phase II), and then cooled at 10° C./min to room temperature. Similar to the sintering of metal powders and other ceramic powders, the sintering temperature, holding time and heating rate could have significant effect of the shrinkage, microstructure and distortion of the final parts. Therefore these parameters were further investigated. The experimental design is shown in Table 5, and the levels of each variable were determined by standard firing schedules used in dental clinics for dental porcelain.

TABLE 5

Heating Variables.

| Factors | Levels |
|---|---|
| Temperature | 750, 800, 850, 900, 925, 950° C. |
| Holding time | Instantaneous (1 min), 10 min., 30 min., 2 h., 10 h |
| Heating rate | 100° C./h, 500° C./h, 5000° C./h |

Sintering of ceramics is a complicated process that involves mass transport driven by multiple mechanisms. For low temperature sintering, the mass transport is mainly controlled by the surface energy and/or interface energy of the ceramic powder. From an atomic diffusion perspective, higher firing temperature or longer holding time would facilitate greater diffusion and therefore promoted the sintering process. In the initial sintering stage, the driving force for diffusion is larger due to the large surface areas. However, as the sintering develops, excessive temperature or holding time might cause excessive grain growth, and the overall properties of sintered parts would deteriorate.

During the first stages of sintering, diffusion occurs mainly through the sintering neck between two contacting particles, which results in shrinkage of the pores and the growing of the neck size between the particles. This in turn causes shrinkage of the part. As diffusion continues, the adjacent grain boundary intersects and forms networks. Driven by surface tension, the grain boundary migrates, and the grains begin to grow. From powder metallurgy theory, the sintering could be roughly estimated by the growth of the sintering neck (R) as a function of sintering temperature (T) and holding time (t).

$$R \propto e{-1/Tt^{1/7}} \quad (1)$$

From equation (1), it was found that the temperature had a pronounced effect on sintering. Therefore, a multi-step experimental design approach was adopted, which was expected to be more efficient and accurate compared to a Taguchi design or full scale design. The multistep experimental design is demonstrated in detail below.

In the first firing temperature step, the effect of fire temperature on the density and microstructure of the samples was investigated, since temperature was the most influential factor on sintering. Table 6 shows the details of this experiment. Each porcelain sample group was fired to temperatures ranging from 750 to 950° C. with 50° C. increments, and held for 30 minutes.

TABLE 6

Firing Temperature Schedule.

| # | Initial temperature | heating rate | Phase I | heating rate | phase II | cooling rate |
|---|---|---|---|---|---|---|
| 1 | RT | 500° C./h | 500° C. × 30 min | 500° C./h | 750° C. × 1 min | 600° C./h |
| 2 | RT | 500° C./h | 500° C. × 30 min | 500° C./h | 800° C. × 1 min | 600° C./h |
| 3 | RT | 500° C./h | 500° C. × 30 min | 500° C./h | 850° C. × 1 min | 600° C./h |
| 4 | RT | 500° C./h | 500° C. × 30 min | 500° C./h | 925° C. × 1 min | 600° C./h |
| 5 | RT | 500° C./h | 500° C. × 30 min | 500° C./h | 950° C. × 1 min | 600° C./h |
| 6 | RT | 500° C./h | 500° C. × 30 min | 500° C./h | 800° C. × 30 min | 600° C./h |
| 7 | RT | 500° C./h | 500° C. × 30 min | 500° C./h | 850° C. × 30 min | 600° C./h |
| 8 | RT | 500° C./h | 500° C. × 30 min | 500° C./h | 900° C. × 30 min | 600° C./h |

In the second holding time step, and from the results from Step 1, the sintering temperature of 850° C. and 900° C. were selected for further investigations. From equation (1) above, the sintering parameters of 850° C.×30 min was selected as the baseline parameters from which a sintering index could be obtained. Experiments were then carried out by considering ±50% and ±20% variation of the sintering index, which was achieved by changing the holding time. Therefore, the range of holding time was estimated to be between 0.2 min and 8.55 h, and the resulting design for holding times at each temperature level were 1 min, 10 min, 30 min, 2 h and 8.6 h, as shown in Table 7.

TABLE 7

Holding time schedule.

| # | Initial temperature | heating rate | Phase I | heating rate | phase II | cooling rate |
|---|---|---|---|---|---|---|
| 2 | RT | 500° C./h | 500° C. × 30 min | 500° C./h | 850° C. × 1 min | 600° C./h |
| 9 | RT | 500° C./h | 500° C. × 30 min | 500° C./h | 850° C. × 10 min | 600° C./h |
| 10 | RT | 500° C./h | 500° C. × 30 min | 500° C./h | 850° C. × 30 min | 600° C./h |
| 11 | RT | 500° C./h | 500° C. × 30 min | 500° C./h | 850° C. × 2 h | 600° C./h |
| 12 | RT | 500° C./h | 500° C. × 30 min | 500° C./h | 850° C. × 8.6 h | 600° C./h |

TABLE 7-continued

Holding time schedule.

| # | Initial temperature | heating rate | Phase I | heating rate | phase II | cooling rate |
|---|---|---|---|---|---|---|
| 13 | RT | 500° C./h | 500° C. × 30 min | 500° C./h | 850° C. × 10 h | 600° C./h |
| 5 | RT | 500° C./h | 500° C. × 30 min | 500° C./h | 900° C. × 1 min | 600° C./h |
| 14 | RT | 500° C./h | 500° C. × 30 min | 500° C./h | 900° C. × 10 min | 600° C./h |
| 15 | RT | 500° C./h | 500° C. × 30 min | 500° C./h | 900° C. × 30 min | 600° C./h |
| 16 | RT | 500° C./h | 500° C. × 30 min | 500° C./h | 900° C. × 2 h | 600° C./h |

In the third heating rate step, because the heating rate affects sintering by promoting or inhibiting grain growth, after an optimal group of temperature and time was obtained from the first two steps, the effect of heating rate was investigated at three levels from slow heating to very rapid heating, as shown in Table 8.

TABLE 8

Heating rate schedule.

| # | Initial temperature | heating rate | Phase I | heating rate | phase II | cooling rate |
|---|---|---|---|---|---|---|
| 17 | RT | 100° C./h | 500° C. × 30 min | 100° C./h | 850° C. × 30 min | 600° C./h |
| 10 | RT | 500° C./h | 500° C. × 30 min | 500° C./h | 850° C. × 30 min | 600° C./h |
| 18 | RT | 5000° C./h | 500° C. × 30 min | 5000° C./h | 850° C. × 30 min | 600° C./h |

Throughout the experiments, the linear shrinkage values were evaluated for each sample, which was calculated according to ASTM C326-09 as:

$$S = [(L_1 - L_2)/L_1] \times 100\% \qquad (2)$$

where S is percentage linear dimensional change, $L_1$ is average length, width, or thickness of specimen before sintering, and $L_2$ is average length, width, or thickness of specimen after sintering. After the parts were sintered, the porosity of each group of specimens was measured using the Archimedes method according to ASTM B962-08 as:

$$R_D = 1 - \rho_e/\rho_n \qquad (3)$$

where $R_D$ is porosity, $\rho_e$ is measured density, and $\rho_n$ is nominal density.

Figure 36:
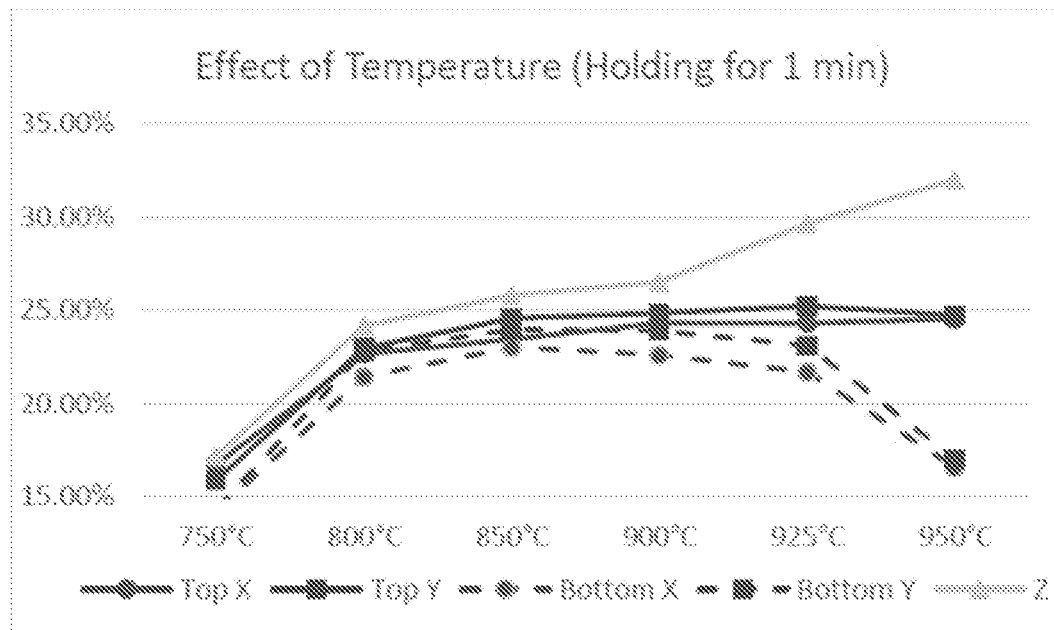
FIG. 36 is a graph showing the trend of linear shrinkage of the fabricated porcelain structures in X, Y and Z building directions as temperature changed (holding for 1 min).

FIG. 36 shows the linear shrinkage of the samples sintered at different temperatures for 1 minute. As sintering temperature increased, the linear shrinkage in horizontal directions (X and Y directions) on the top surface of the sintered parts showed an ascending trend until 850° C., and then remained largely constant at about 25%. However, the curve of the linear shrinkage in horizontal directions at the bottom surface showed an obvious decrease after a small peak of linear shrinkage at 850° C. It could be speculated that the glassy phase has a lower melting point, which led to reduction in porosity and enhanced densification of the body. On the other hand, at elevated temperature the glass phase might partially collapse under its own gravity due to the loss of strength. This also explained the shrinkage phenomenon in the vertical direction (Z direction), which showed an ongoing ascending trend as the temperature increases, with the maximum value up to 32% (at 950° C.).

Figure 37:
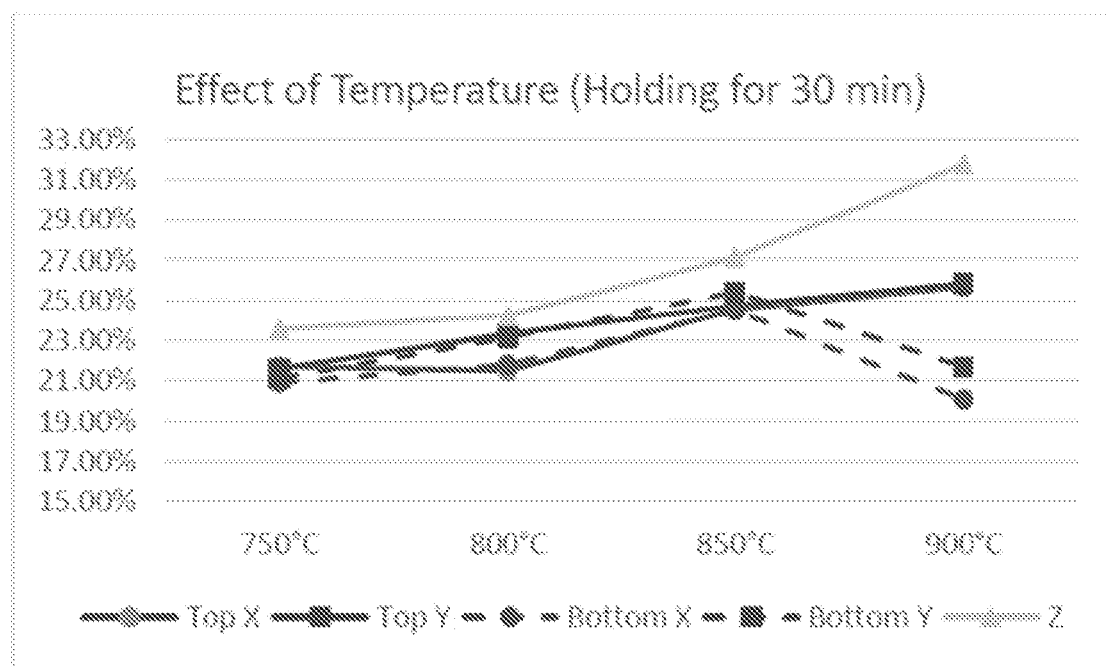
FIG. 37 is a graph showing the trend of linear shrinkage of the fabricated porcelain structures in X, Y and Z building directions as temperature changed (holding for 30 min).

In the group of specimens which were sintered for 30 minutes (FIG. 37), the linear shrinkage in horizontal directions on the top surface kept increasing after 850° C. When the temperature increased to the next level (925° C.), the sintered body showed apparent signs of melting. At 950° C., the specimen completely lost its original cubic shape due to melting. The linear shrinkage on the bottom surface appeared to reach maximum at 850° C. before it started to decrease, which was similar to the group sintered for 1 minute.

Figure 38:
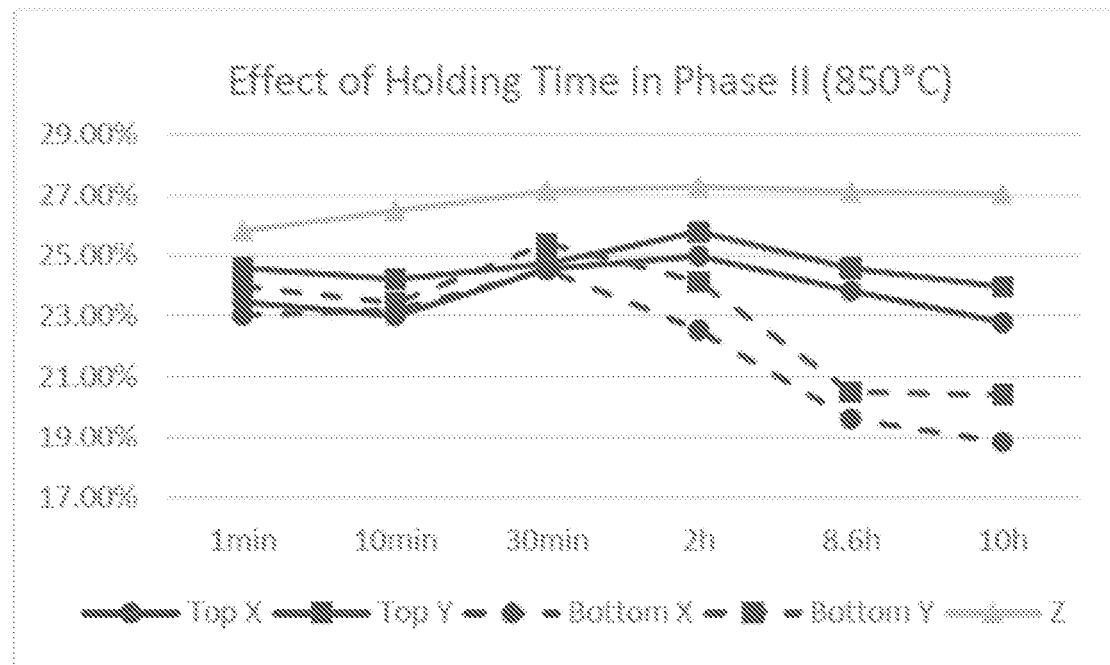
FIG. 38 is a graph showing the trend of linear shrinkage of the fabricated porcelain structures in X, Y and Z building directions as holding time changed (sintering at 850° C.).

For the group sintered at 850° C., the linear shrinkage showed a slight increasing trend with longer sintering time until the holding time reached 2 hours, and the linear shrinkage started to decrease on the top surface of horizontal directions with longer holding time (FIG. 38). The linear shrinkage at the bottom of horizontal directions also had the same trend except that the maximum appeared at the holding time of 30 min. On the other hand, the linear shrinkage in the vertical direction exhibited more or less constant linear shrinkage. The apparent decrease of linear shrinkage at prolonged sintering times could be explained by the sintering dynamics. When sintering developed to the late stage in which the pores are completely enclosed and become spherical, further sintering no longer effectively eliminates the porosity. Instead, under the thermal diffusion effect, the pores could start to migrate and coalesce, which could potentially lead to macro-scale distortion of the sintered structures.

Figure 39:
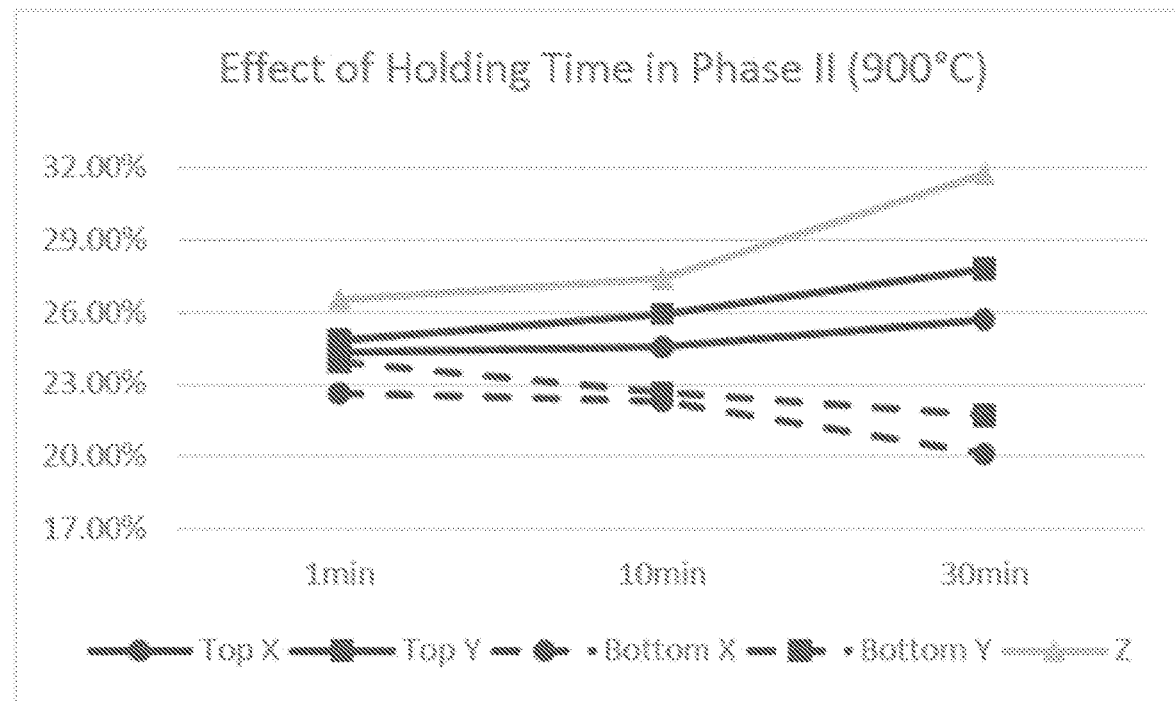
FIG. 39 is a graph showing the trend of linear shrinkage of the fabricated porcelain structures in X, Y and Z building directions as holding time changed (sintering at 900° C.).
Figure 40:
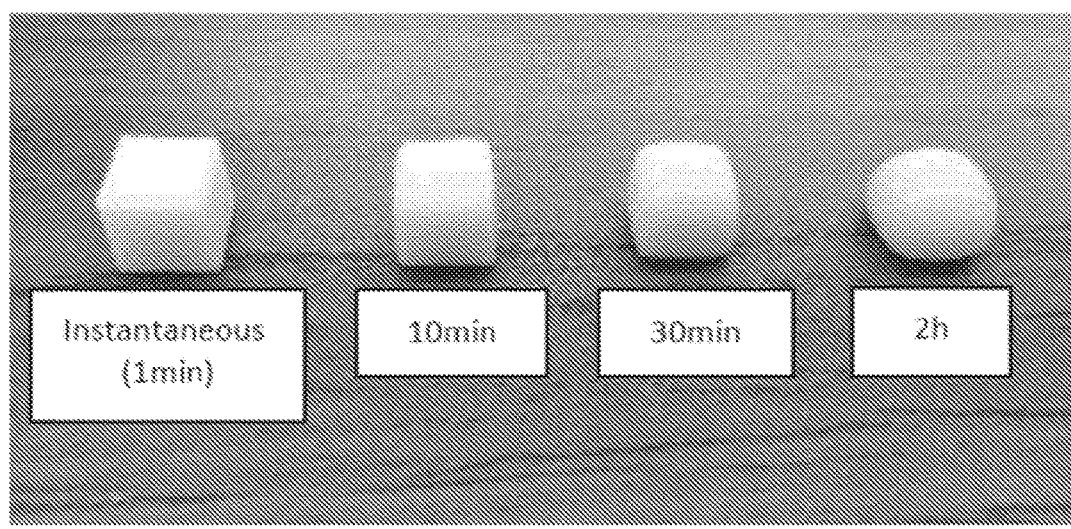
FIG. 40 is an image of porcelain specimens sintered at 900° C. for different holding times.

For the group of specimens sintered at 900° C. as shown in FIG. 39, excessive sintering was apparent beyond 1 minute of holding time. This was also clearly shown in the shapes of the final parts, as partial melting and part distortion became obvious at longer holding times (FIG. 40).

Figure 41:
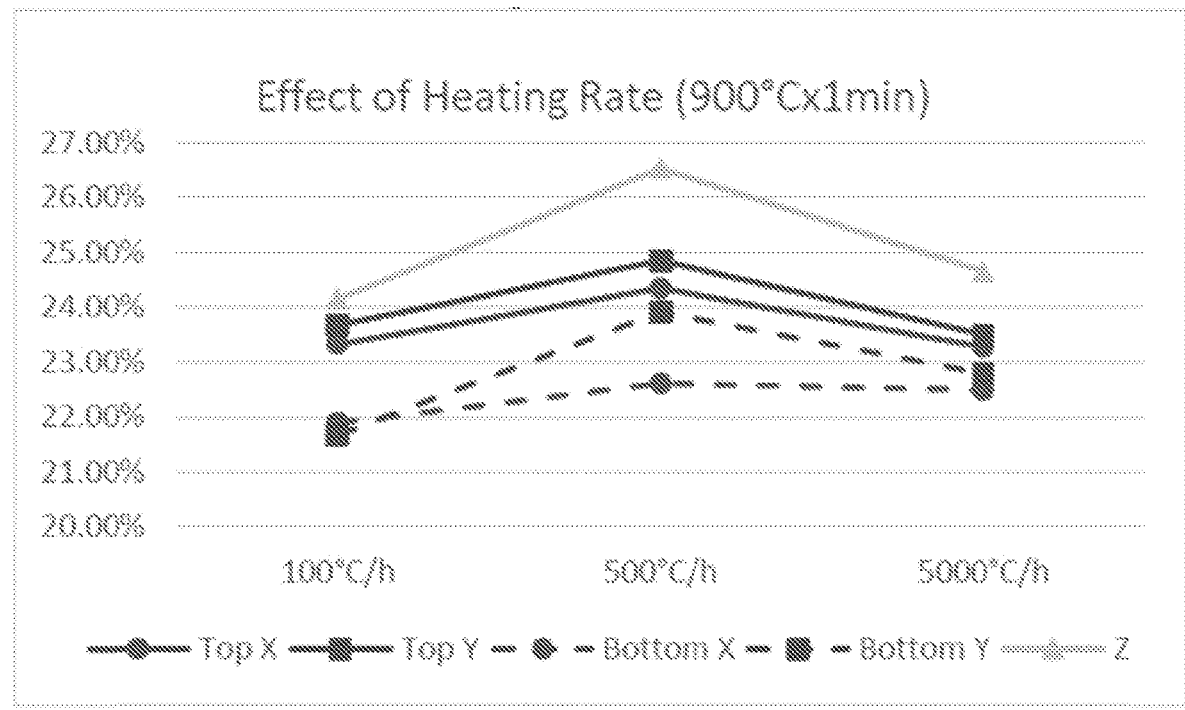
FIG. 41 is a graph showing the linear shrinkage of the fabricated porcelain structures in X, Y and Z building directions at different heating rates.

The heating rate experiment described above was performed at 900° C. for 1 minute, and the results of the linear shrinkage are shown in FIG. 41. The linear shrinkage in all directions showed the same trend as the heating rate changed from 100° C./h to 5000° C./h. Generally, the vertical direction had larger shrinkage than horizontal directions, and the top surface also had a little higher values than the bottom surface.

For very rapid heating rate (5000° C./h), smaller linear shrinkage could be expected due to the insufficient sintering. On the other hand, at very slow heating rate (100° C./h), the samples were in fact subject to prolonged holding time at high temperature ranges, which might effectively cause gravity induced distortion and over-sintering distortion as discussed before.

Figure 42A:
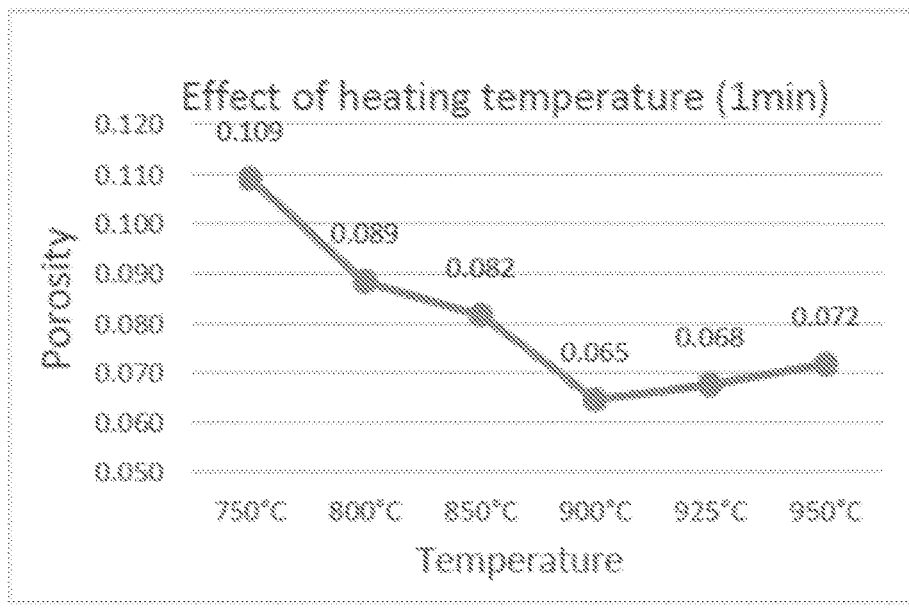
FIGS. 42A-42B are graphs showing the porosity effect of heating temperature in the fabricated porcelain structures after heating for 1 min (FIG. 42A) and for 30 min (FIG. 42B).
Figure 42B:
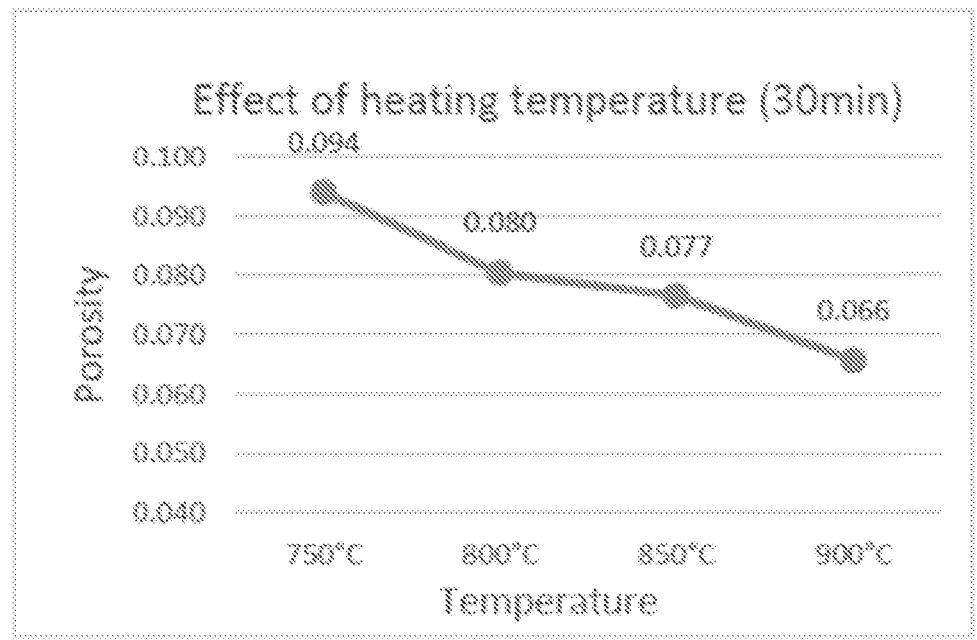

As shown in FIGS. 42A-42B, as the sintering temperature increased, the porosity of the final part reduced steadily due to more sufficient sintering. Also, at 925° C./30 min significant melting already occurred, therefore it appeared that the minimum porosity attainable porosity with the current process method was about 7% for the dental porcelain.

Figure 43A:
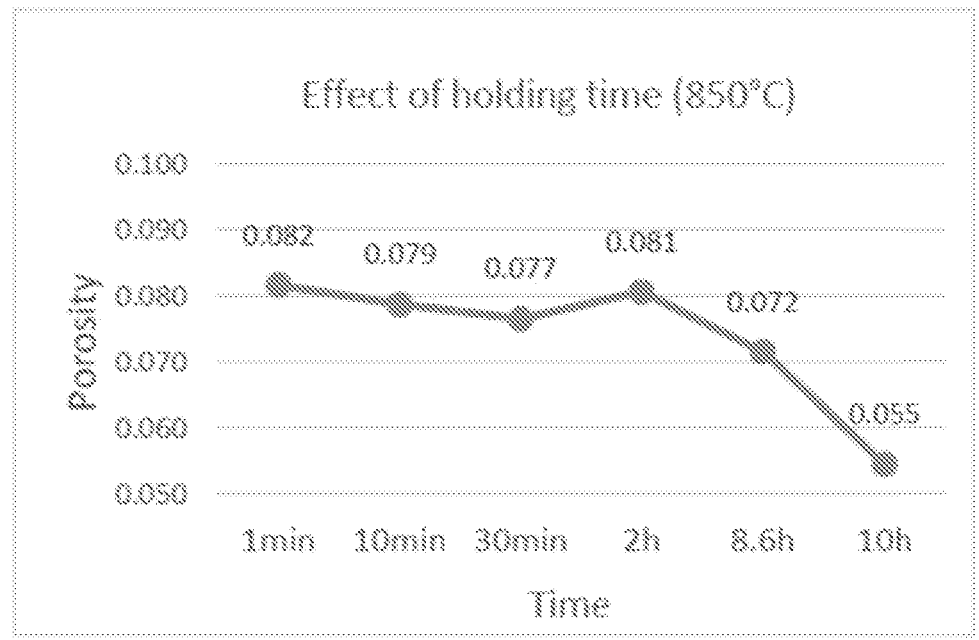
FIG. 43A-43B are graphs showing the porosity effect of holding time in the fabricated porcelain structures at temperatures of 850° C.
Figure 43B:
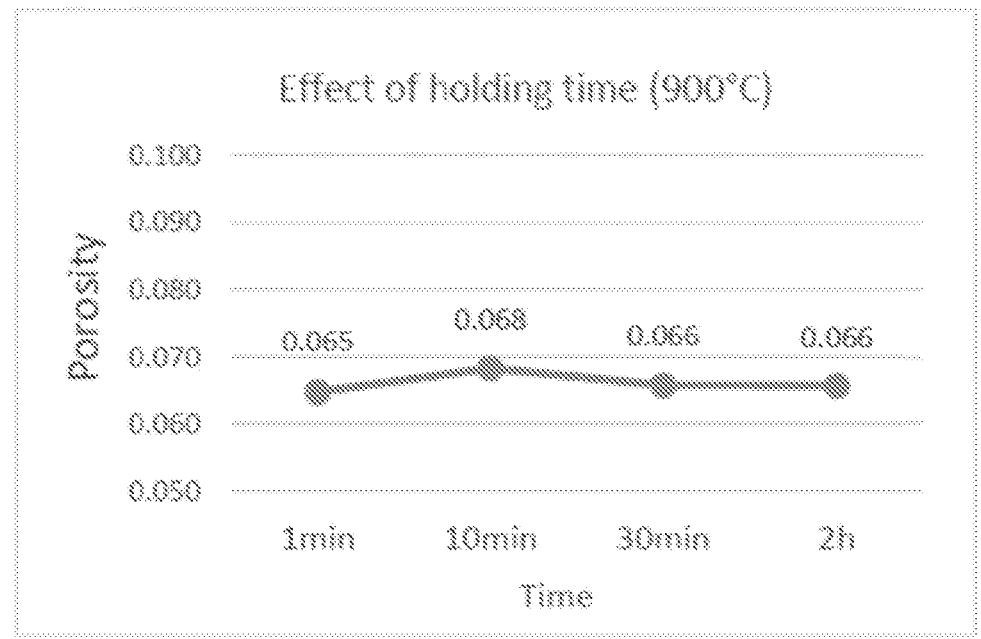

As shown in FIGS. 43A-43B, the holding time did not appear to have significant effect on the porosity at both 850° C. and 900° C. When the holding time was shorter than 2 hours, the porosity did not change significantly at different holding times. However, when the holding time was longer than 2 hours, the porosity values showed apparent decrease. This is in agreement with the linear shrinkage observed at these temperature levels. This observation also implied that when sintered at proper sintering temperatures, the holding time of the parts could be shortened considerably without significantly affecting the overall porosity, which is very useful for reducing the total production time for dental ceramic structures.

Figure 44:
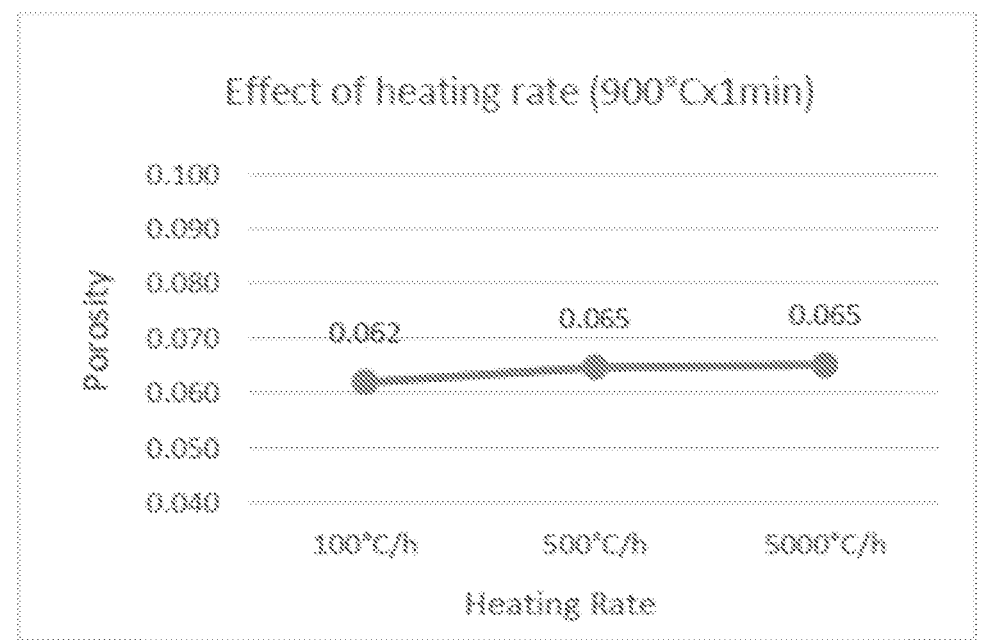
FIG. 44 is a graph showing the porosity effect of heating rate in the fabricated porcelain structures.

There was no significant effect of heating rate on porosity as shown in FIG. 44, which was unexpected since the linear shrinkage of samples at 5000° C./h heating rate was significantly lower. A possible reason could be that those samples exhibit some through-porosity due to the insufficient sintering, which resulted in water infiltration into the interior of the samples during the weight measurement.

Figure 45:
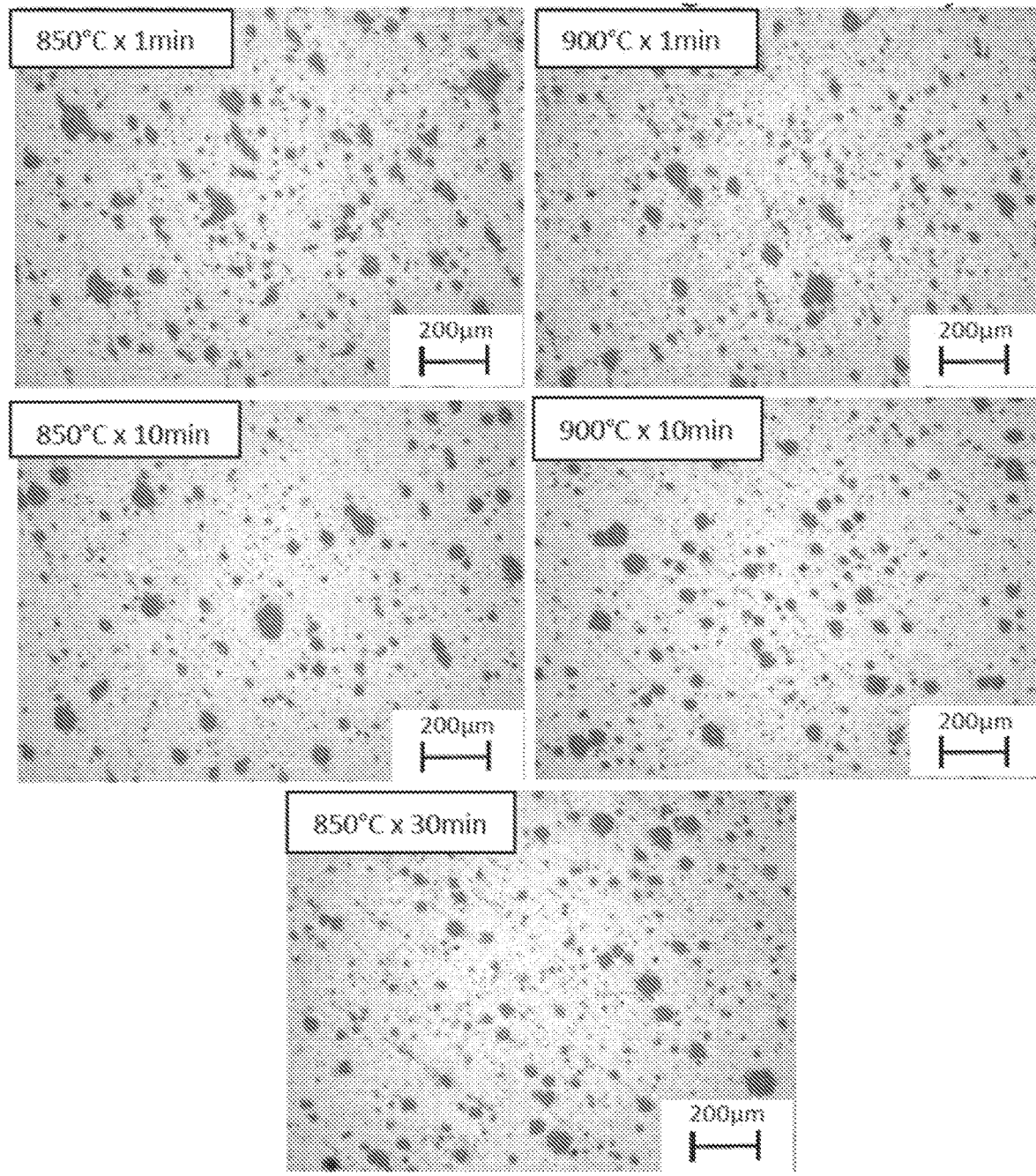
FIG. 45 includes images showing the distribution of pores in the fabricated porcelain structures as viewed by optical microscopy (shrinkage stable).
Figure 46:
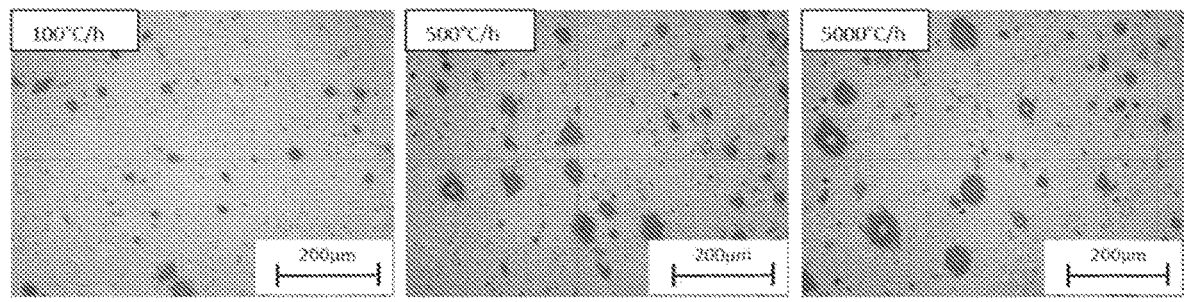
FIG. 46 includes images showing the distribution of pores in the fabricated porcelain structures at varying heating rates.

From the foregoing results, it was believed that the linear shrinkage and porosity could keep a relative stability at 850° C. for 1-30 min and 900° C. for 1-10 min, which is also illustrated by the microscopy of these samples as shown in FIG. 45. In general, as sintering developed, the pore morphology and size distribution should become more homogenous, which could also be seen from the microscopy. The microscopy from the heating rate experiment samples are also indicative, as larger porosity and pore size distribution as a result of insufficient sintering could be clearly seen from FIG. 46.

Figure 47:
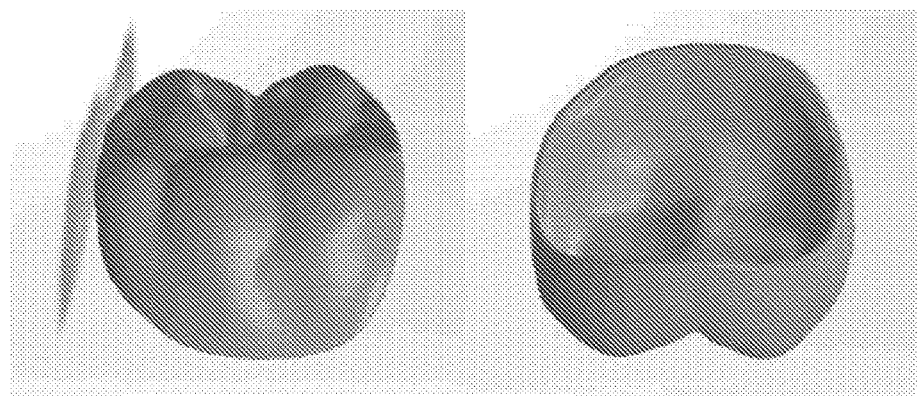
FIG. 47 is a 3D digital model of a dental crown prosthesis made in accordance with the presently-disclosed subject matter.
Figure 48:
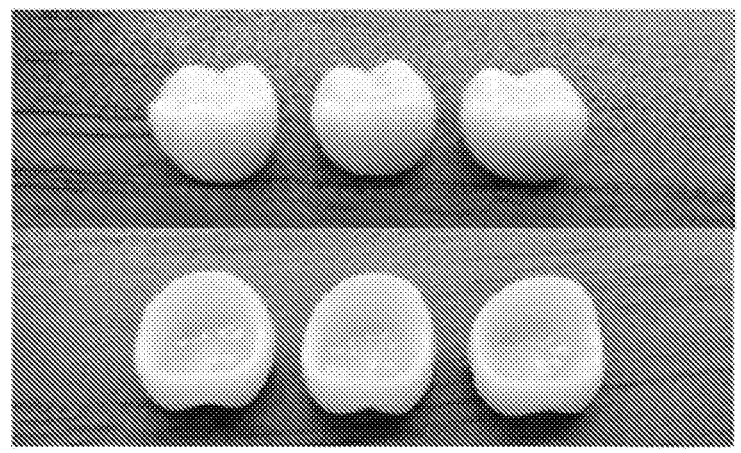
FIG. 48 includes images of porcelain crowns made in accordance with the presently-disclosed subject matter.

As recognized by those in the art, a dental crown is a tooth-shaped cap that is placed over a tooth to cover the tooth and improve its appearance, and thin wall features are commonly designed inside of crown structures. Based on the experimental results obtained from the foregoing studies, a batch of dental ceramic crown prostheses from a scanned model were printed using the ExOne M-Lab system using the optimal method with relatively stable linear shrinkage. The 3D model was rescaled 40% larger than the original scanned model to obtain the correct size after shrinkage. The rescaled 3D model of a dental crown prosthesis is shown in FIG. 47. The linear shrinkages in each direction (X, Y and Z directions) in the dental crown were studied. FIG. 48 shows the final parts that were printed using processing parameters of 50% saturation and 60% power level, and sintered at 900° C. for 1 minute.

Figure 49:
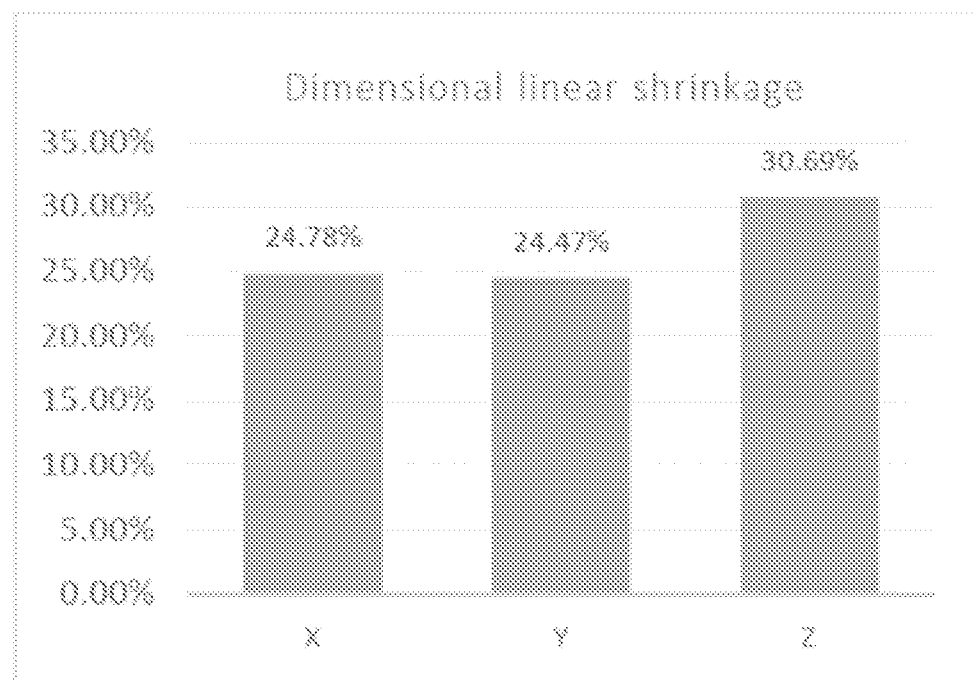
FIG. 49 is a graph showing the linear shrinkage in X, Y and Z directions of dental crowns made in accordance with the presently-disclosed subject matter.

The average linear shrinkage values in each of three directions of the fabricated dental crowns are shown in FIG. 49. The linear shrinkage in the Z (vertical) direction was larger than X and Y (horizontal) directions. The lateral shrinkage values were similar to the experimental results obtained from the cubic specimens. However, the linear shrinkage value in the Z direction was 15% larger than the results from the cubic specimens. This might be caused by the partial collapse of the structure during sintering. Since the crown prosthesis has thin wall features, when the green parts were placed in the furnace upside down, slight gravity induced distortion might have occurred at the crown surfaces. Furthermore, with Archimedes method, the porosity was measured to be an average value of 5.7%, which is in good agreement with the cubic specimens.

Figure 50:
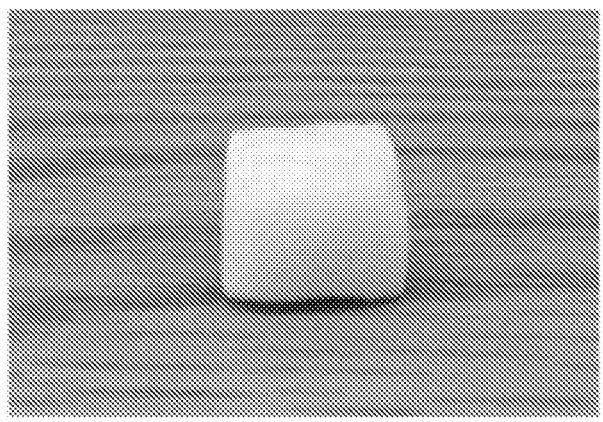
FIG. 50 is an image of a cubic porcelain specimen fabricated by a standard manual methods.
Figure 51:
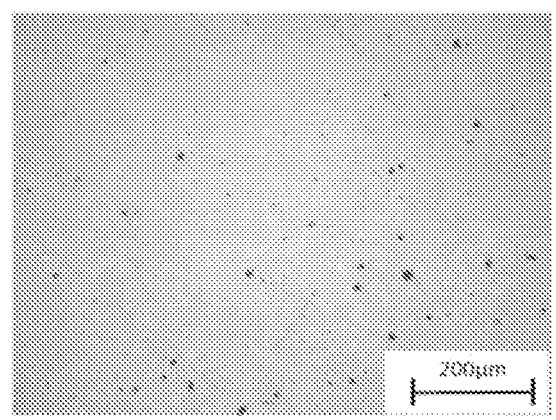
FIG. 51 is an image showing a microstructure of a cubic porcelain specimen fabricated by a standard manual method.

For comparison purposes, a cubic specimen with the same dimensions was also fabricated with the standard method currently used in dentistry. The specimen was made by manually forming the cubic shape from the wetted InLine porcelain powder, which was then sintered using the standard firing schedule (900° C. for 1 minute, heating rate 500° C./hour). FIG. 50 shows the sintered specimen. The geometrical accuracy of the fabricated specimen was not very good, which might be caused by the manual manipulation during the fabrication. The porosity of this specimen was 3.3%, which was lower than the ones fabricated using the 3DP process. FIG. 51 shows the distribution of pores under optical microscopy, and the image confirmed its lower porosity.

As one of the less well understood types of additive manufacturing (AM) processes, the 3DP process has a number of control parameters that can significantly affect the fabrication quality. The experimental studies described above revealed the relationships between these parameters and the geometrical accuracy and microstructure of the final parts for a dental porcelain ceramic powder. More specifically, and in summary: 1) flow agent had a significant effect on aggregation reduction, and improved flowability significantly for the printing process; 2) when saturation was set above 60%, the green parts began to deform under the friction of the roller, but when saturation was as low as 45%, the binder could not provide enough strength to bind the powder, and additionally, saturation had a significant effect on the pores of sintered parts in micrographs as pore diameters decreased as the saturation level increased, while total porosity did not seem to be significantly affected; 3) power level did not have a significant effect on geometry and microstructure of the green and final parts; 4) in terms of the effect of temperature, when distortion did not occur, linear shrinkage in horizontal directions increased as the temperature increases, but, at higher temperature, parts were more likely to exhibit gravity induced distortion, therefore reducing the accuracy of the part; 5) in terms of the effect of holding time, the holding time had a very mild effect on the linear shrinkage and porosity of the parts as, at higher temperature levels, longer holding time could result in significant distortion of the parts, but, on the other hand, the surface finish could be improved with longer holding time; 6) in terms of the effect of heating rate, the overall heating rate had a significant effect on the linear shrinkage of the parts, which was primarily caused by the amount of sintering at different heating rates, and revealed that, at a very rapid heating rate (5000° C./h), a longer holding time would be necessary in order to avoid insufficient sintering; 7) the process parameters obtained from the cubic specimens were successfully applied to a thin-walled dental crown prosthesis, which exhibited good agreement of linear shrinkage values in all three directions; and 8) binder jetting 3DP processes can produce better dimensional accuracies compared to the current standard fabrication methods, but the higher porosity level in the final parts could affect the mechanical performance of the dental ceramic structures produced by 3DP.

Throughout this document, various references are mentioned. All such references are incorporated herein by reference, including the references set forth in the following list:

REFERENCES

1. H. J. Conrad, W. J. Seong, I. J. Pesun. Current ceramic materials and systems with clinical recommendations. Journal of Prosthetic Dentistry. 98(2007): 389-404.
2. I. Denry, J. A. Holloway. Ceramics for Dental Applications: A Review. Materials. 3(2010): 351-368.

3. Rizkalla A S, Jones D W. Mechanical properties of commercial high strength ceramic core materials. Dent Mater. 2004; 20:207-12.
4. Rizkalla A S, Jones D W. Indentation fracture toughness and dynamic elastic moduli for commercial feldspathic dental porcelain materials. Dent Mater. 2004; 20:198-206.
5. P. C. Guess, S. Schultheis, E. A. Bonfante, P. G. Coelho, J. L. Ferencz, N. R. F. A. Silva. All-Ceramic Systems: Laboratory and Clinical Performance. Dental Clinics of North America. 55(2011): 333-352.
6. S. D. Heintze, V. Rousson. Survival of Zirconia- and Metal-supported Fixed Dental Prostheses: A Systematic Review. Introductory Journal of Prosthodontics. 6(2010): 493-502.
7. A. J. Raigrodski, M. B. Hillstead, G. K. Meng, K. H. Chung. Survival and Complications of Zirconia-based Fixed Dental Prostheses: A Systematic Review. Journal of Prosthetic Dentistry. 107(2012): 170-177.
8. I. Sailer, A. Fehér, F. Filser, I. J. Gauckler, H. Luthy, C. H. Hammerle. Five-year clinical results of zirconia frameworks for posterior fixed partial dentures. Introductory Journal of Prosthodontics. 20(2007): 383-388.
9. S. Schwarz, C. Shroder, A. Hassel, W. Bomicke, P. Rammelsberg. Survival and Chipping of Zirconia-based and Metal-ceramic Implant-supported Single Crowns. Clinical Implant Dentistry and Related Research. 14(2011): 119-125.
10. L. H. He, M. W. Swain. Enamel-A Functionally graded natural coating. Journal of Dentistry. 37(2009): 596-603.
11. B. An, R. Wang, D. Arola, D. Zhang. The role of property gradients on the mechanical behavior of human enamel. Journal of the Mechanical Behavior of Biomedical Materials. 9(2012): 63-72.
12. Y. Zhang, H. Chai, B. R. Lawn. Graded Structures for All-ceramic restorations. Journal of Dental Research. 89(2010): 417-421.
13. Y. Zhang, J.-W. Kim. Graded structure for damage resistant and aesthetic all-ceramic restorations. Dental Materials. 25(2009): 781-790.
14. Y. Zhang, L. Ma. Optimization of ceramic strength using elastic gradients. Acta Materialia. 57(2009): 2721-2729.
15. Y. Zhang. Overview: Damage resistance of graded ceramic restorative materials. Journal of the European Ceramic Society. 32(2012): 2623-2632.
16. Y. Zhang, M-J. Sun, D. Zhang. Designing functionally graded materials with superior load-bearing properties. Acta Biomaterialia. 8(2012): 1101-1108.
17. R. Nathan Katz. Advanced ceramic (Dental ceramic). Nov. 21, 2000.
18. I. Gibson, D. W. Rosen, B. Stucker. Additive Manufacturing Technologies: Rapid Prototyping to Direct Digital Manufacturing. Springer, New York, N.Y., 2009.
19. N. Harlan, S-M. Park, D. L. Bourell, J. J. Beaman. Selective laser sintering of zirconia with micro-scale features. Proceedings of the $10^{th}$ Solid Freeform Fabrication Symposium, Austin, Tex., USA, 1999.
20. H. Wnag, D. L. Bourell, J. J. Beaman. Selective laser sintering of quartz powder. Proceedings of the $8^{th}$ Solid Freeform Fabrication Symposium, Austin, Tex., USA, 1997.
21. F. Klocke, H. Wirtz. Selective laser sintering of zirconium silicate. Proceedings of the $9^{th}$ Solid Freeform Fabrication Symposium, Austin, Tex., USA, 1998.
22. H. B. Denham, J. Cesarano, B. H. King. Mechanical behavior of robocast alumina. Proceedings of the $9^{th}$ Solid Freeform Fabrication Symposium, Austin, Tex., USA, 1998.
23. C. Dai, G. Qi, S. Rangarajan, S. Wu, N. A. Langrana, A. Safari, S. C. Danforth. High quality, fully dense ceramic components manufactured using fused deposition of ceramics (FDC). Proceedings of the $8^{th}$ Solid Freeform Fabrication Symposium, Austin, Tex., USA, 1997.
24. R. A. Levy, T-M. G. Chu, J. W. Halloran, S. E. Feinberg, S Hollister. CT-generated porous hydroxyapatite orbital floor prosthesis as a prototype bioimplant. American Journal of Neuroradiology. 18(1997): 1522-1525.
25. M. J. Cima, M. Oliveira, H. R. Wang, E. Sachs, R. Holman. Slurry-based 3DP and fine ceramic components. Proceedings of the $12^{th}$ Solid Freeform Fabrication Symposium, Austin, Tex., USA, 2001.
26. S. Uhland, R. Holman, B. DeBear, P. Saxton, M. Cima, E. Sachs. Three-dimensional printing, 3DP, of electronic ceramic components. Proceedings of the $10^{th}$ Solid Freeform Fabrication Symposium, Austin, Tex., USA, 1999.
27. L. Yang, S. Zhang, G. Oliveira, B. Stucker. Development of a 3D printing method for production of dental application. Proceedings of the $24^{th}$ Solid Freeform Fabrication Symposium, Austin, Tex., USA, 2013.
28. T. R. Jackson, H. Liu, N. M. Patrikalakis, E. M. Sachs, M. J. Cima. Modeling and designing functionally graded material components for fabrication with local composition control. Materials and Design. 20(1999): 63-75.
29. Y. Zhang, M.-J. Sun, D. Zhang, Designing functionally graded materials with superior load-bearing properties. Acta Biomaterialia. 8(2012): 1101-1108.
30. F. F. Noecker, J. N. Dupont. Functionally Graded Copper—Steel Using Laser Engineered Net Shaping Process. Proceedings of the $13^{th}$ Solid Freeform Fabrication Symposium, Austin, Tex., USA, 2002.
31. C. Gasdaska, R. Clancy, M. Ortiz, V. Jamalabad, A. Virkar, D. Popovitch. Functionally Optimized Ceramic Structures. Proceedings of the $9^{th}$ Solid Freeform Fabrication Symposium, Austin, Tex., USA, 1998.
32. M. A. Fafari, W. Han, F. Mohammadi, A. Safari, S. C. Danforth, N. Langrana. A novel system for fused deposition of advanced multiple ceramics. Rapid Prototyping Journal. 692000): 161-174.
33. Li-Hong He, Zi-Hong Yin, Ludwig Jansen van Vuuren, Elizabeth A. Carter, Xiu-Weng Liang. A natural functionally graded biocomposite coating—human enamel. Acta Biomaterialia. 9(5), 2003: 6330-6337.
34. Jones D W., "Development of dental ceramics: an historical prospective", Dent Clin N 29: 621-644.
35. Barreiro M. M, Riesgo O, Vicente E. E, "Phase identification in dental porcelains for ceramo-metallic restorations", Dent Mater 5: 51-7.
36. O'Brien W J. "Dental porcelain, Ch. 21 in: Dental materials: Properties and selection", Quintessence, Chicago, 1989.
37. Denry I., Holloway A., "Ceramics for dental applications: A review", Mat 3: 351-368.
38. Anusavice K J, "Dental Ceramics. Phillip's Science of Dental Materials", 12th Ed., Sounders.
39. Conrad H. J., Seong W.-J. I. Pesun J. "Current ceramic materials and systems with clinical recommendations: a systematic review", Journal of Prosthetic Dentistry. 98: 389-404.
40. Piddock V, "Evaluation of a New High-Strength Aluminous Porcelain", Clinical Materials 4: 349-360
41. McLean J W., "The science and art of dental ceramics I: The nature of dental ceramics and their clinical use", Quintessence, Chicago, 1979.

42. Philips R W. "Dental Ceramics, C H. 26 in Skinner's science of dental Materials", 9th Ed, WB Saunders.
43. Combe E C., "Notes on dental materials", 6th ED. Churchill Livingstone.
44. Jones D W., "Materials for fixed and removable prosthodontics, Ch. 13 in: Williams D F, material science and technology", 5th ED, Weinheim.
45. Burke F J, Lucarotti P S, "Ten-year outcome of crowns placed with in the General Dental Services in England and Wales", J Dent 37:12-24.
46. Rekow E D, Silva NRFA, Coelho P G, Zhang Y, Guess P, Thompson V P, "Performance of dental ceramics: challenges for improvements", J Dent Res 90:937-952.
47. Pjetursson B E, Sailer I, Zwahlen M, Hammerle C H, "A systemic review of the survival and complication rates of all-ceramic and metal-ceramic reconstructions", J Dent Reg 90:938-986.
48. Thompson V J, Rekow E D, "Dental ceramics. In: Bioceramics and their clinical applications", 1st ED, London.
49. Valenti M, Valenti A, "Retrospective survival analysis of 261 lithium disilicate crowns in a private general practice", Quintessence Int 40: 573-579.
50. Whittneben J G, Write R F, Weber H P, Gallucci G O, "A systematic review of the clinical performance of CAD/CAM single-tooth restorations", Int J Prosthodont 22:466-471.
51. Zhang Y, Kim J W, "Graded structures for damage resistant and aesthetic all-ceramic restorations", Dent Mater 25: 781-790.
52. Yang L., Zhang S., Oliveira G., Stucker B., "Development of a 3D printing method for production of dental application. Proceeding of Solid Freeform Fabrication (SFF)", Symposium, 2013.
53. Zhang S., Yang L., Zandinejad A., Miyanaji H., Stucker B., An experimental study of ceramic dental porcelain materials using a 3D print (3DP) process. Proceeding of Solid Freeform Fabrication (SFF) Symposium, 2014.
54. Gonzaga C C, Yoshimura H N, Cesar P F, Miranda Jr W G., "Subcritical crack growth in porcelains, glass—ceramics, and glass-infiltrated alumina composite for dental restorations", J Mater Sci Mater Med 20: 1017-24.
55. Fairhurst C W, Lockwood P E, Ringle R D, Twiggs S W.' "Dynamic fatigue of feldspathic porcelain", Dent Mater 9: 269-73.
56. Yoshimura H N, Cesar P F, Miranda W G, Gonzaga C C, Okada C Y, Goldenstein H., "Fracture toughness of dental porcelains evaluated by IF, SCF, and SEPB methods", Am Ceram Soc 88: 1680-3.
57. J. Li, H. Liao and L. Hermansson, Sintering of partially-stabilized zirconia and partially-stabilized zirconia—hydroxyapatite composites by hot isostatic pressing and pressureless sintering, Biomaterials, 17 (1996), 1787-1790.
58. Itoh H, Wakisaka Y, Ohnuma Y, Kuboki Y, A new porous hydroxyapatite ceramic prepared by cold isostatic pressing and sintering synthesized flaky powder. Dental Materials Journal, 13 (1994), 25-35.
59. Isabelle Denry and Robert Kelly, State of the art of zirconia for dental applications. Dental Materials, 24 (2008), 299-307.
60. Massimo Martorelli, Salvatore Gerbino, Michele Giudice, Pietro Ausiello, A comparison between customized clear and removable orthodontic appliances manufactured using RP and CNC techniques, 29 (2013), e1-e10.
61. Saralasrita Mohanty, Arun Prabhu Rameshbabu, Santanu Dhara, Net shape forming of green alumina via CNC machining using diamond embedded tool. 39 (2013), 8985-8993.
62. I. Gibson, D. W. Rosen, B. Stucker. Additive Manufacturing Technologies: Rapid Prototyping to Direct Digital Manufacturing. Springer, New York, N.Y., 2009.
63. M Wu, J Tinschert, M Augthun, I Wagner, J Schadlich-Stubenrauch, P. R Sahm, H Spiekermann. Application of laser measuring, numerical simulation and rapid prototyping to titanium dental castings. Dental Materials, 17 (2001), 102-108.
64. Abbas Azari and Sakineh Nikzad, The evolution of rapid prototyping in dentistry: a review. Rapid Prototyping Journal, 15 (2009), 216-225.
65. Jiwen Wang, Leon Shaw and Thomas Cameron, Solid Freeform Fabrication of permanent dental restorations via slurry micro-extrusion. Journal of the American Ceramic Society, 89 (2006), 346-349.
66. J. Ebert, E. Ozkol, A. Zeichner, K. Uibel, O. Weiss, U. Koops, R. Telle, H. Fischer. Direct Inkjet Printing of Dental Prostheses Made of Zirconia, Journal of Dental Research. 88(2009): 673-676.
67. Alaadien Khalyfa, Sebastian Vogt, Jurgen Weisser, Gabriele Grimm, Annett Rechtenbach, Wolfgang Meyer, Matthias Schnabelrauch, Development of a new calcium phosphate powder-binder system for the 3D printing of patient specific implants. 18 (2007), 909-916.
68. C. X. F Lama, X. M Moa, S. H Teoha, D. W Hutmacher, Scaffold development using 3D printing with a starch-based polymer. 20 (2002), 49-56.
69. Scientific documentation IPS InLine system, 2010.
70. Li Yang, Shanshan Zhang, Gustavo Oliveira, Brent Stucker, Development of a 3D Printing Method for Production of Dental Application. Proceedings of the 24th International Solid Freeform Fabrication Symposium. Austin, Tex., USA. 2013.
71. Aerosil R 972 Hydrophobic fumed silica MSDS.
72. Peiyun Huang, Powder metallurgy principle, 2nd edition. Metallurgy Industrial press, 1997.
73. A. B. Spierings, M. Schneider. Comparison of density measurement techniques for additive manufactured metallic parts. Rapid Prototyping Journal, 17(5), 2011, 380-386.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of fabricating a dental restoration, comprising the steps of:
    (a) providing a powder of a dental material;
    (b) selectively depositing an amount of a binder onto the powder of the dental material to produce an unfinished layer of the dental material;
    (c) repeating steps (a) and (b) to produce a three-dimensional unfinished model, wherein selectively depositing the amount of binder onto the powder of the dental material comprises increasing the amount of binder deposited onto the powder at each layer;
    (d) sintering the unfinished model to produce a three-dimensional dental restoration having a functionally-graded structure, wherein the dental restoration includes an outer enamel-like portion having a plurality of layers and an inner dentin-like portion having a plurality of layers, wherein the dental restoration consists of a width extending from the outermost layer of the outer enamel-like portion to the innermost layer of the inner dentin-like portion, and wherein a hardness and an elastic modulus of the dental restoration reduces at each layer across the width of the dental restoration from the outermost layer to the innermost layer.

2. The method of claim 1, wherein the dental material comprises a ceramic.

3. The method of claim 1, wherein providing a powder of a dental material comprises deploying a layer of powder via a powder deploy mechanism.

4. The method of claim 3, wherein the powder deploy mechanism is a rotating roller.

5. The method of claim 1, wherein providing a powder of a dental material comprises varying an amount of powder of the dental material provided to produce a layer of dental material having a portion with an elasticity, hardness, or porosity different than that of an adjacent portion.

6. The method of claim 1, further comprising a step of curing the binder prior to repeating step (a) and/or prior to sintering the unfinished model.

7. The method of claim 6, wherein the step of curing the binder comprises subjecting the binder to thermal radiation, ultraviolet radiation, or both.

8. The method of claim 6, wherein curing the binder comprises varying an amount of time the binder is cured to produce a layer of dental material having a portion with an elasticity, hardness, or porosity different than that of an adjacent portion.

9. The method of claim 1, wherein the binder includes one or more organic compositions, inorganic compositions, surfactants, dispersants, and combinations thereof.

10. The method of claim 9, wherein selectively depositing a binder onto the powder of the dental material further comprises varying the amount of inorganic compositions included in the binder to produce a layer of dental material having a portion with an elasticity, hardness, or porosity different than that of an adjacent portion.

11. The method of claim 9, wherein the inorganic compositions comprise iron oxide particles.

12. The method of claim 1, wherein selectively depositing a binder onto the powder of the dental material is performed by an inkjet printing platform.

13. The method of claim 1, wherein the amount of the binder selectively deposited onto the powder of dental material is sufficient to produce a binder saturation level of about 45% to about 75%.

14. The method of claim 1, wherein steps (a) and (b) are repeated about 10 to about 1,000 times.

15. The method of claim 1, wherein sintering the functionally-graded structure comprises heating the unfinished model to a temperature of about 750° C. to about 950° C.

16. The method of claim 1, wherein sintering the functionally-graded structure comprises heating the unfinished model to a temperature of about 500° C. for a first predetermined time period, and subsequently heating the unfinished model to a temperature of about 750° C. to about 950° C. for a second predetermined time period.

17. The method of claim 16, wherein the first predetermined time period is about 30 min and the second predetermined time period is about 1 min to about 9 hrs.

18. The method of claim 1, wherein the outer enamel-like portion includes an outer portion and an inner portion and wherein the outer portion of the enamel-like portion has an elastic modulus of about 100 GPa to about 140 GPa and a hardness of about 0.8 GPa to about 1.2 GPa, and wherein the inner portion of the enamel like-portion has an elastic modulus of about 40 GPa to about 80 GPa and a hardness of about 0.4 GPa to about 0.8 GPa.

19. The method of claim 1, wherein the dentin-like portion has an elastic modulus of about 15 GPa to about 45 GPa across the width of the dentin-like portion.

20. The method of claim 1, wherein an amount of binder selectively deposited at step (b) increases by 0.1% from an adjacent preceding layer.

21. A dental restoration produced by the process according to claim 1.

22. A method of fabricating a dental restoration, comprising the steps of:
(a) providing a powder of a dental material;
(b) selectively depositing an amount of a binder sufficient to produce a binder saturation level of about 45% to about 75% onto the powder of the dental material to thereby produce an unfinished layer of the dental material;
(c) curing the binder;
(d) repeating steps (a) to (c) to produce a three-dimensional unfinished model, wherein selectively depositing the amount of binder onto the powder of the dental material comprises increasing the amount of binder deposited onto the powder at each layer; and
(e) heating the unfinished model to a first temperature of about 500° C. for a first predetermined time period and to a second temperature of about 750° C. to about 950° C. for a second predetermined time period to produce a three-dimensional dental restoration having a functionally-graded structure, wherein the dental restoration includes an outer enamel-like portion having a plurality of layers and an inner dentin-like portion having a plurality of layers, wherein the dental restoration consists of a width extending from the outermost layer of the outer enamel-like portion to the innermost layer of the inner dentin-like portion, and wherein a hardness and an elastic modulus of the dental restoration reduces at each layer across the width of the dental restoration from the outermost layer to the innermost layer.

23. The method of claim 22, wherein the first predetermined time period is about 30 min and the second predetermined time period is about 1 min to about 9 hrs.

24. The method of claim 22, wherein an amount of binder selectively deposited at step (b) increases by 0.1% from an adjacent preceding layer.

* * * * *